US007563776B2

(12) United States Patent
Federico

(10) Patent No.: US 7,563,776 B2
(45) Date of Patent: Jul. 21, 2009

(54) COMPOSITIONS COMPRISING FUSION POLYPEPTIDES HIV-NEF AND NGF, AND METHODS OF USING THE SAME

(75) Inventor: Maurizio Federico, Rome (IT)

(73) Assignee: Istituto Superiore di Sanita, Rome (IT)

( * ) Notice: Subject to any disclaimer, the term of this patent is extended or adjusted under 35 U.S.C. 154(b) by 86 days.

(21) Appl. No.: 10/651,836

(22) Filed: Aug. 29, 2003

(65) Prior Publication Data

US 2004/0087537 A1 May 6, 2004

(30) Foreign Application Priority Data

Sep. 19, 2002 (GB) .................................. 0221778.4

(51) Int. Cl.
 *A01K 43/04* (2006.01)
 *A61K 31/70* (2006.01)
 *A01N 63/00* (2006.01)
 *A01N 65/00* (2006.01)
 *C12N 15/00* (2006.01)
 *C12N 5/00* (2006.01)
 *C12N 5/02* (2006.01)

(52) U.S. Cl. .................... 514/44; 424/93.1; 424/93.21; 435/320.1; 435/325

(58) Field of Classification Search ........................ None
See application file for complete search history.

(56) References Cited

U.S. PATENT DOCUMENTS 6,312,682 B1 * 11/2001 Kingsman et al. .......... 424/93.2

OTHER PUBLICATIONS

D'Aloja, et al. (1998) J. Virol., 72(5): 4308-19.*
Bowie, et al. (1990) Science, 247 : 1306-10.*
Rudinger (1976) Peptide Hormones, University Park Press, Baltimore, MD., pp. 1-7.*
Kappes, et al. (2002) Somatic Cell and Molecular Genetics, 26(1-6): 147-58.*
Sellon, et al. (1996) Veterinary Microbiology, 53: 209-21.*
Jeeninga, et al. (2000) Journal of Virology, 74(8): 3740-51.*
Arrighi, et al. (2001) Experimental Hematology, 29: 1029-37.*
Adachi et al., *J. Virol.*, 59(2):284-291 (1986).
Aiken et al., *Cell*, 76:853-864 (1994).
Alessandrini et al., *J. Gen. Virol.*, 81:2905-2917 (2000).
An et al., *J. Virol.*, 73(9), 7671-7677 (1999).
Baur et al., *Immunity*, 1:373-384 (1994).
Baur et al., *Immunity*, 6:283-291 (1997).
Bona et al., *Gene Ther.*, 4:1085-1092 (1997).
Bukovsky et al., *J. Virol.*, 73(8):7087-7092 (1999).
Burns et al., *Proc. Natl. Acad. Sci. USA*, 90:8033-8037 (1993).
Chadwick et al., *Gene Ther.*, 7:1362-1368 (2000).
Chelucci et al., *Blood*, 85(5):1181-1187 (1995).
Chen et al., *J. Virol.*, 71(7):5495-5504 (1997).
Chowers et al., *J. Virol.*, 68(5):2906-2914 (1994).
Conlon et al., *J. Immunol.*, 149(10):3278-3289 (1992).
Cuturi et al., *J. Exp. Med.*, 165:1581-1594 (1987).
Duh et al., *Proc. Natl. Acad. Sci. USA*, 86:5974-5978 (1989).
Dull et al., *J. Virol.*, 72(11):8463-8471 (1998).
Emerman et al., *Cell*, 57:1155-1165 (1989).
Fackler et al., *Molecular Cell*, 3:729-739 (1999).
Federico et al., *J. Gen. Virol.*, 74:2099-2110 (1993).
Federico et al., *Virology*, 206:76-84 (1995).
Follenzi et al., *Nat. Genet.*, 25:217-222 (2000).
Fox et al., *Hum. Gene Ther.*, 6:997-1004 (1995).
Fraisier et al., *Gene Ther.*, 5:946-954 (1998).
Grignani et al., *Cancer Res.*, 58:14-19 (1998).
Hamm et al., *J. Virol.*, 73(7):5741-5747 (1999).
Jang et al., *Genes Dev.*, 4:1560-1572 (1990).
Jia et al., *Leuk. Res.*, 19(3):187-194 (1995).
Lavigne et al., *Biochem. Biophys. Res. Commun.*, 237:566-571 (1997).
Lindsten et al., *Science*, 244:339-343 (1989).
Liu et al., *Gene Ther.*, 1:32-37 (1994).
Malim et al., *Nature*, 338:254-257 (1989).
Mangasarian et al., *Immunity*, 6:67-77 (1997).
Mautino et al., *J. Virol.*, 75(8):3590-3599 (2001).
Mhashilkar et al., *EMBO J.*, 14(7):1542-1551 (1995).
Mhashilkar et al., *Hum. Gene Ther.*, 10:1453-1467 (1999).
Naldini et al., *Science*, 272:263-267 (1996).
Piguet et al., *EMBO J.*, 17(9):2472-2481 (1998).
Plavec et al., *Gene Ther.*, 4:128-139 (1997).
Re et al., *Prog. Cell Cycle Res.*, 3:21-27 (1997).
Roebuck et al., *Gene Expr.*, 8:67-84 (1999).
Rossi et al., *Ann. NY Acad. Sci.*, 511:390-400 (1987).
Rossi et al., *Gene Ther.*, 4:1261-1269 (1997).
Rossi, *Adv. Drug Deliv. Rev.*, 44:71-78 (2000).
Sawai et al., *J. Biol. Chem.*, 270(25):15307-15314 (1995).
Shahabuddin et al., *Antisense Nucleic Acid Drug Dev.*, 10:141-151 (2000).
Subbramanian et al., *J. Exp. Med.*, 187(7):1103-1111 (1998).
Sung et al., *J. Exp. Med.*, 167:937-953 (1988).
Theodore et al., *AIDS Res. Hum. Retroviruses*, 12(3):191-194 (1996).
Vodicka et al., *Genes Dev.*, 12:175-185 (1998).
Wigler et al., *Cell*, 16:777-785 (1979).

* cited by examiner

*Primary Examiner*—Robert M Kelly
(74) *Attorney, Agent, or Firm*—Marshall, Gerstein & Borun LLP

(57) ABSTRACT

A conjugate comprising a first and second sequence, wherein the first sequence comprises at least part of the human low affinity Nerve Growth Factor receptor (LNGFR) or a polynucleotide coding for LNGFR, and the second sequence comprises at least part of a mutant HIV Nef or a polynucleotide coding for F12Nef.

28 Claims, 9 Drawing Sheets

COMPOSITIONS COMPRISING FUSION POLYPEPTIDES HIV-NEF AND NGF, AND METHODS OF USING THE SAME

The present application claims the benefit of priority of GB 0221778.4, which was filed Sep. 19, 2002. The entire text of the aforementioned application is specifically incorporated herein by reference.

FIELD OF THE INVENTION

The present invention relates to a conjugate and its use in a method of imparting resistivity to infection by HIV, including superinfection by HIV.

BACKGROUND OF THE INVENTION

Several strategies of anti HIV intracellular immunization have been attempted over the last decade. These include the expression of either HIV-1 trans dominant proteins (i.e. Rev, Tat) (Fox et al., 1995; Fraiser et al, 1998; Hamm et al., 1999; Liu et al., 1994; Mautino et al., 2001; Plavec et al., 1997; Rossi et al., 1997), HIV-1 antisense sequences (Chadwick and Lever, 2000; Lavigne and Thierry, 1997; Shahabuddin and Khan, 2000), ribozymes targeting HIV-1 sequences (for a review, see Rossi, 2000), or intrabodies against HIV-1 proteins (Mhashilkar et al., 1995; Mhashilkar et al., 1999). An HIV-1 nef allele (F12nef) whose expression in trans (D'Aloja et al., 1998), or in cis (Olivetta et al., 2000) potently inhibits the HIV-1 replication was recently isolated and characterized. This anti HIV-1 phenotype strictly depends on the presence of three rare amino acid substitutions (i.e. G140E, V153L, and E177G) (D'Aloja et al., 2001). F12Nef acts against HIV-1 in both the processing of p55Gag polyprotein (Fackler et al., 2001), and the viral assembly/release (Olivetta et al., 2000). The consequence is that, as best described in the in cis expression system, the infecting HIV-1 becomes totally unable to release even non infectious viral particles (Olivetta et al., 2000). F12Nef is defective for a number of functions described for wild type Nef. In particular, it does not down regulate neither CD4 (D'Aloja et al., 1998), nor Class I major histocompatibility complex (MHC) membrane expression (M. Doria, personal communication), it does not activate the Nef associated kinase (NAK/PAK) (D'Aloja et al., 2001; Nunn and Marsh, 1996; Renkema et al., 1999; Sawai et al., 1994), and fails to interact with the V1H subunit of the V-ATPase (D'Aloja et al., 2001; Lu et al., 1998). On the other hand, F12Nef maintains the ability to dispose at the cell margin, as well as to interact with the CD4 intracytoplasmic tail, being both functions required for its antiviral phenotype (Olivetta et al., 2000).

However, the success of a gene engineering protocol relies on the sustained expression of both the transgene of interest and the gene selection marker. Frequently, this was attempted by inserting them under the control of different promoters. Unfortunately, this strategy frequently led to an unbalanced activity of the two promoters, due to the promoter interference. Considering that transduced cells are generally selected on the basis of the marker expression, unsatisfactory levels of the transgene expression could be often encountered.

The present invention seeks to overcome this problem and provide a means to selected cells with have been transduced with the transgene of interest and thus to provide a more efficient way to treat HIV infection.

SUMMARY OF THE INVENTION

The expression of the HIV-1 Nef triple mutant F12Nef strongly inhibits HIV-1 replication. This unique feature was exploited in a novel anti HIV-1 gene therapy design by constructing an HIV-1 Tat defective lentivirus vector expressing the product of fusion between the low affinity human Nerve Growth Factor receptor truncated in its intracytoplasmic domain (ΔLLNGFR, NH$_2$ moiety), and F12Nef (COOH moiety), under the control of the HIV-1 long terminal repeats. In this manner, both the selection marker (ΔLLNGFR) and the anti HIV-1 effector are comprised in the same fusion protein, whose expression is targetable by HIV-1 infection. Such a vector was proved to transduce human cells efficiently and, upon HIV-1 infection, it expressed high levels of the fusion protein. In addition, a strong antiviral activity of the ΔLNGFR/F12Nef expressing vector was demonstrated in cell lines as well as in primary cell cultures challenged with T- or M-tropic HIV-1 isolates. Thus, the HIV-1 targetable expression of the ΔLNGFR/F12Nef fusion protein represents a both novel and powerful tool for an effective anti HIV-1 gene therapy strategy.

According to one aspect of the present invention there is provided a conjugate comprising a first sequence and a second sequence, wherein the first sequence comprises at least part of a low affinity Nerve Growth Factor receptor (LNGFR) or a polynucleotide coding therefor, and the second sequence comprises at least part of a mutant HIV Nef or a polynucleotide coding therefor.

In a particularly preferred embodiment, the LNGFR is the human LNGFR.

Preferably the conjugate is in the form of a fusion protein or a polynucleotide encoding therefor.

Preferably the LNGFR forms the NH2 part of the fusion protein and the mutant HIV Nef forms the COOH part of the fusion protein.

Preferably the LNGFR is truncated, more preferably the LNGFR is truncated (ΔLNGFR) in its intracytoplasmic domain.

Preferably the mutant HIV Nef contains one or more of the following amino acid substitutions: G140E, V153L and E177G, more preferably the mutant HIV Nef contains the amino acid substitution G140E, and most preferably the mutant HIV Nef contains all three amino acid substitutions (F12Nef).

According to another aspect of the present invention there is provided a polynucleotide sequence encoding the conjugate of the present invention.

According to another aspect of the present invention there is provided a retroviral vector comprising, and capable of expressing, the polynucleotide of the present invention.

Preferably the retroviral vector is derivable from a lentiviral vector, and even more preferably the lentiviral vector is derivable from HIV.

Preferably the polynucleotide is operably linked to a viral LTR.

Preferably the viral LTR is desensitised to activation by TNFα.

Preferably the LTR is desensitised by deleting or mutating the NF-kB binding sites in the LTR.

In one embodiment the retroviral vector is in the form of an integrated provirus.

According to another aspect of the present invention there is provided a retroviral particle obtained or obtainable from the retroviral vector of the present invention.

According to another aspect of the present invention there is provided a retroviral production system for producing the retroviral vector or the particle of the present invention comprising the retroviral vector of the present invention and retroviral gag-pol, and Env.

Preferably the retroviral gag-pol and Env are in different vectors.

Preferably in the retroviral production system of the present invention HIV Vpr is expressed and/or the system further comprises at least part of the sequence from a HIV pol polypurine tract (PPT).

According to another aspect of the present invention there is provided a retroviral vector or retroviral particle produced by the retroviral production system of the present invention.

Preferably the retroviral particle of the present invention is pseudotyped.

According to another aspect of the present invention there is provided a cell infected or transduced with a polynucleotide, a conjugate, a retroviral vector or retroviral particle of the present invention.

Preferably the cell is a monocyte, macrophage or lymphocyte.

Preferably the cell is activated. Activation may be achieved by HIV superinfection, e.g. through HIV Rev or the cell may be activated by TNFα.

According to another aspect of the present invention there is provided a polynucleotide, a conjugate, a retroviral vector, a retroviral particle or a cell of the present invention for use in medicine.

According to another aspect of the present invention there is provided a pharmaceutical composition provided a polynucleotide, a conjugate, a retroviral vector, a retroviral particle or a cell of the present invention and a pharmaceutically acceptable carrier, diluent or excipient.

According to yet another aspect of the present invention there is provided use of provided a polynucleotide, a conjugate, a retroviral vector, a retroviral particle or a cell of the present invention for the preparation of a medicament for treatment or prevention of HIV infection or related conditions.

Thus, the present invention provides a method of treating or preventing HIV infection or related conditions comprising administering to a patient in need of the same an effective amount of provided a polynucleotide, a conjugate, a retroviral vector, a retroviral particle or a cell of the present invention.

According to a further aspect of the present invention there is provided a method of treating or preventing HIV infection of a related condition comprising infecting or transducing a cell with provided a polynucleotide, a conjugate, a retroviral vector or a retroviral particle of the present invention Preferably the infecting or transducing is carried out ex vivo and the cell is introduced in a patient.

BRIEF DESCRIPTION OF THE FIGURES

(FIG. 3A) ΔLNGFR membrane expression in CEMss HN and NF cell populations. CEMss stably transduced with HN or NF vectors were analyzed for the membrane expression of ΔLNGFR by FACS. Non transduced CEMss cells labeled with anti ΔLNGFR mAb served as control (Ctrl). MFI of each cell population are indicated. The MFI of the three cell populations upon labeling with species and isotype matched IgG ranged 1-1.5. (FIG. 3B) HIV-1 Gag/ΔLNGFR double florescence FACS analysis of HIV-1 infected CEMss cell populations. CEMss (Ctrl), CEMss HN, and CEMss NF cells were infected with 0.5 MOI of NL4-3 HIV-1 strain and, after four days, were analyzed for the simultaneous expression of HIV-1 Gag related products and ΔLNGFR membrane expression. The MFI values for the ΔLNGFR expression in HIV-1 positive HN and NF transduced cell populations are indicated. Quadrants were set on the basis of the fluorescence levels of double labeled uninfected parental CEMss cells. Percentages of cells scored for each quadrant are reported as well. (FIG. 3C) ΔLNGFR FACS analysis of CEMss HN and NF cells untreated or treated with 10 ng/mL of TNFα for 16 hr. MFI of each cell population are indicated. Non transduced CEMss cells labeled with anti ΔLNGFR mAb (MFI 1-1.5) served as control (Ctrl), and scored similarly to control cells treated with TNFα. The MFI of each cell population upon labeling with species and isotype matched IgG ranged 1-1.5. (FIG. 3D) Western blot analysis for the detection of the ΔLNGFR/F12Nef fusion protein. Proteins from total cell extracts of both untreated and TNFα treated CEMss NF cells were resolved by electrophoresis, and transferred on a filter membrane. This was incubated with an anti Nef sheep antiserum and, in a second incubation step, with HRP-protein G. Signals were revealed with the ECL method. Uninfected and NL4-3 HIV-1 infected CEMss cells were used as controls. Nef specific products are indicated on the left side, whereas molecular size markers are reported on the right. (FIG. 3E) ΔLNGFR membrane expression in CEMss HN cells upon anti TNFα Abs treatment. CEMss HN cells were treated for 16 hr with a dose of anti TNFα Abs able to neutralize up to 50 ng/mL of human TNFα, or with an equivalent amount of specie specific, irrelevant IgG, and the ΔLNGFR membrane expression was measured by FACS analysis. As control, parental CEMss cells also were analyzed for the ΔLNGFR membrane expression (Ctrl). MFI of untreated CEMss HN cells overlapped that from cells treated with unspecific IgG.

(FIG. 4A) CD4 FACS analysis on CEMss HN and NF cells and, as control, on parental CEMss cells (Ctrl). Each cell population was labeled with a FITC conjugated anti CD4 mAb (b) or, as control, with a FITC conjugated species and isotype matched IgG (a).

(FIG. 5A) Cell membrane ΔLNGFR FACS analysis on PBLs 48 hr after the transduction with HN or NF lentivirus vectors. Purified human PBLs were stimulated with PHA for 48 hr. Afterwards, they underwent two cycles of transduction with 5 ng of each vector for $10^5$ cells. After additional 48 hr of recovery, cells were analyzed for the cell membrane ΔLNGFR expression. As control, non transduced PBLs from the same donors were utilized (Ctrl). Results refer to transduction experiments performed on cells from two donors (a, b).

(FIG. 6A) ΔLNGFR membrane expression in human PBLs three days after the positive immunoselection for the ΔLNGFR expression. The FACS analyses were performed in cells from three different donors (a-c). MFI values are reported for cells from donor a. Non transduced PBLs labeled with anti LNGFR mAb served as controls (Ctrl). The MFI values of each cell population upon labeling with species and isotype matched IgG overlapped that of ΔLNGFR labeled control PBLs.

(FIG. 9A) HIV-1 Gag/ΔLNGFR double florescence FACS analysis of HN or NF transduced MDM. Six days after the purification, MDM were transduced with the HN or NF vectors, and, after additional five days, infected with 5 ng/$10^5$ cells of (VSV-G) pseudotyped Δenv HIV-1. Non transduced MDM from the same donor were used as control cells (Ctrl). Quadrants were set considering the fluorescence levels of either the parental or the transduced uninfected parental MDM.

SUMMARY OF SEQUENCE LISTING

Figure 1:
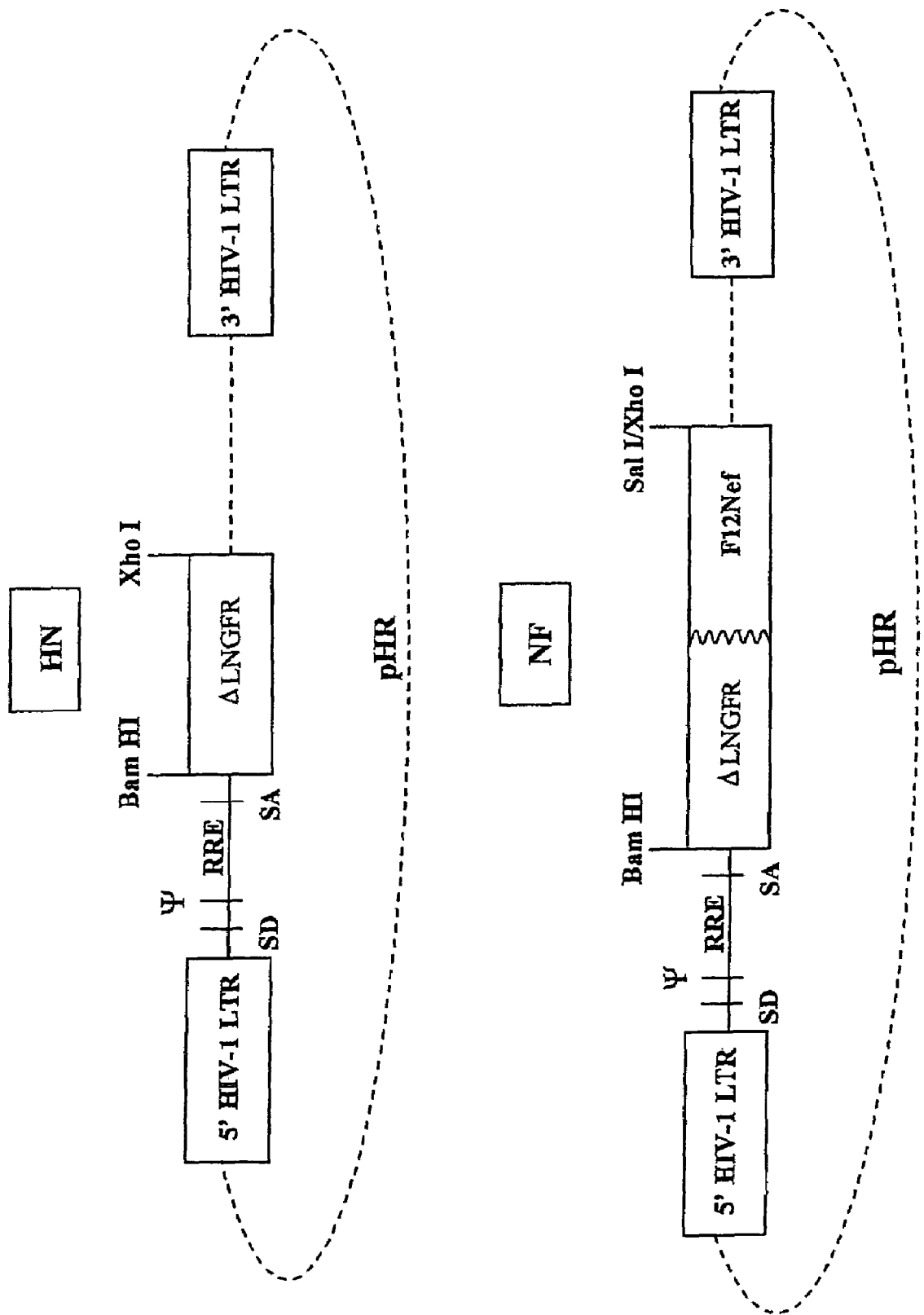
FIG. 1. is a schematic map of ΔLNGFR based lentivirus vectors. Both ΔLNGFR and ΔLNGFR/F12Nef transgenes were inserted in the Bam HI/Xho I cloning sites of the pHRprime lentivirus vector. The splice acceptor (SA) and donor (SD) sites, the Rev Responsive Elements (RRE), the packaging signal (Ψ), and the position of both 5' and 3' HIV-1 LTRs are indicated.

SEQ ID NO.1 shows the amino acid sequence for the human LNGFR receptor precursor (NCBI ID: P08138) which may be used in the present invention.

SEQ ID NO.2 shows an example of a polynucleotide sequence of a truncated human LNGFR (Δ LNGFR) which may be used in the present invention.

SEQ ID NO.3 shows an example of a polynucleotide sequence coding for a fusion protein consisting of the truncated LNGFR and NefF12 (Δ LNFGR-NefF12) which may be used in the present invention.

SEQ ID NO.4 shows an example of a polypeptide sequence of a truncated human LNGFR protein (Δ LNGFR protein) which may be used in the present invention. Amino acids 1-279 of the ΔLNFGR-NefF12 fusion protein (SEQ ID NO. 6) correspond to amino acids 40-319 of this sequence.

SEQ ID NO.5 shows the polypeptide sequence of Nef protein from HIV1-clone 12 Nef12 (NCBI ID: P04324) which may be used in the present invention.

SEQ ID NO.6 shows an example of a polypeptide sequence of a ΔLNFGR-NefF12 fusion protein which may be used in the present invention—the ΔLNGFR portion of this protein (amino acid 1-276) aligns with amino acid 1-276 of human LNGFR (SEQ. ID No. 1) whilst the NefF12 portion of this fusion protein (Amino acid 281-486) of this protein aligns with amino acid 1-206 of HIV1 Nef (SEQ ID No.5).

SEQ ID NO.7 shows the polynucleotide sequence of the human LNGFR and codes for SEQ ID NO:1.

SEQ ID NO.8 shows an example of a polynucleotide sequence for a mutant Nef F12 which may be used in the present invention—the protein sequence for which is given in SEQ ID NO 9.

SEQ ID NO.9 shows an example of a polypeptide sequence for a mutant NefF12 protein which may be used in the present invention. This sequence contains 3 amino acid changes when compared to the HIV1 Nef protein: G140E, V153L and E177G. Amino acids 281-486 of the ΔLNFGR-NefF12 fusion protein (SEQ ID NO. 6) correspond to amino acids 1-206 of this sequence.

DETAILED DESCRIPTION OF THE PREFERRED EMBODIMENTS

Various preferred features and embodiments of the present invention will now be described by way of non-limiting example.

The practice of the present invention will employ, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; J. M. Polak and James O'D. McGee, 1990, *In Situ Hybridization: Principles and Practice*; Oxford University Press; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* Methods in Enzymology, Academic Press. Each of these general texts is herein incorporated by reference.

The antiviral property of the HIV-1 F12Nef mutant (D'Aloja et al., 1998; D'Aloja et al., 2001; Fackler et al., 2001; Olivetta et al., 2000) was exploited in a novel design of anti HIV-1 gene therapy based on the expression of the ΔLNGFR/F12Nef fusion protein regulated by the HIV-1 LTR in the context of a lentivirus vector. ΔLNGFR/F12Nef is a bi-functional chimeric protein, i.e. it acts at the same time as a selection marker, and as an anti HIV-1 effector. This represents a great benefit in the perspective of a therapeutic application, as the marker perfectly identifies cells expressing the anti HIV-1 transgene, thus facilitating both the selection and the monitoring of transduced cells.

Conjugate

The present invention relates to a conjugate which is a molecule comprising at least one low affinity human Nerve Growth Factor receptor (LNGFR) protein or polynucleotide encoding therefor (for ease of reference this may be referred to as the first sequence or marker) linked to at least one mutant HIV Nef or polynucleotide encoding therefor (for ease of reference this may be referred to as the second sequence or effector) formed through genetic fusion or chemical coupling. Thus, conjugates include fusion proteins in which the marker protein is linked to a mutant HIV Nef via their polypeptide backbones through genetic expression of a DNA molecule encoding these proteins, directly synthesised proteins and coupled proteins in which pre-formed sequences are associated by a cross-linking agent. The term is also used herein to include associations, such as aggregates, of the mutant HIV Nef with the marker protein. According to one embodiment the second sequence may comprise a polynucleotide sequence. This embodiment may be seen as a protein/nucleic acid complex.

The conjugates of the present invention are capable of being bound by or taken up by a population of HIV target cells so that an effector function corresponding to the second polypeptide sequence coupled can take place within the cell when it is infected or superinfected by HIV. In addition, target cells transduced with the mutant HIV Nef may be efficiently selected.

As mentioned above, previous attempts to select transduced cells had met with difficulties. The present invention provides a single entity which is capable of both as a selection marker and as an effective anti-HIV product.

The term "HIV target cell" includes cells which are capable of being infected or superinfected either in vitro or in vivo by HIV. Such cells are preferably human cells. HIV target cells include lymphocytes (T cells), monocytes and macrophages.

The term "effector function" includes resistivity, i.e. the ability to resist infection or superinfection by a virus, in particular a retrovirus, and preferably HIV.

The term "superinfection" includes the ability of a virus to infect a cell already infected by a virus.

Thus in a preferred embodiment of the present invention the conjugate in the form of a polynucleotide sequence is delivered to a population of the target cells in a viral vector. The polynucleotide sequence which integrates, preferably stably, into at least some of the target cells is capable of being expressed to confer resistance to superinfection by a second virus. The second virus may or may not be derived from the same virus as the viral vector.

Preferably the polynucleotide sequence integrates into at least 1% of cell nuclear genomes. More preferably the polynucleotide sequence integrates into about 1% to 10% of cell nuclear genomes.

Target Cell

As mentioned above the conjugate of the present invention may be delivered to a target cell. Preferably, the animal cell is a cell of the immune system, e.g., a T-cell. Preferably the cell is a cell of the human immune system. Even more preferably the cell is a cell which is capable of being infected by HIV, i.e. an HIV permissible cell. The conjugate may also be introduced into ex vivo cells to study the effects of HIV encoded proteins on the physiology of such cells. Thus, cells into which the conjugate may be introduced include peripheral blood lymphocytes, monocytes, macrophages, astrocytes.

Human Low Affinity Nerve Growth Factor (LNGFR)

The common neutrophin receptor, low affinity Nerve Growth Factor gene (LNGFR) (also referred to as NGFR and p75NTR) is not expressed on the majority of human hematopoietic cells, thus allowing quantitative analysis of transduced gene expression by immunofluorescence, with single cell resolution. Thus, fluorescence activated cell sorter analysis of expression of LNGFR may be performed in transduced cells to study gene expression. Further details on analysis using LNGFR may be found in Mavilio 1994.

When the conjugate of the present invention is in the form of a fusion protein the LNGFR preferably forms the $NH_2$ moiety of the fusion protein. This may be achieved by tagging the COOH terminus of the LNGFR with F12Nef.

The present invention in one embodiment makes use of a truncated LNGFR (also known as ΔLNGFR). Preferably the LNGFR is truncated in its intracytoplasmic domain and is described in Mavilio 1994. As mentioned below, the present invention also encompasses the use of variants, derivatives, analogues, homologues and fragments of the LNGFR.

Mutant HIV Nef

The human immunodeficiency virus/simian immunodeficiency virus (HIV/SIV) Nef protein is a regulatory protein with a molecular mass of between about 27 and 34 kDa and which is expressed in large amounts in infected cells and arises early in the virus replication cycle. Nef is targeted to the cell membrane. Nef seems to act at two levels: it increases the efficiency of proviral synthesis, as demonstrated in quiescent peripheral blood lymphocytes (PBL) and plays a role in virus particle release. On the other hand, evidence demonstrates that Nef is a multifunctional protein that interacts with different cellular protein partners. In particular, Nef down-regulates CD4 by both accelerating its internalisation rate and reducing recruitment if CD4-containing clathrin-coated pits for routing to lysosomes. Through distinct genetic determinants, Nef down-regulates major histocompatibility complex (MHC) class I molecules, mainly by misrouting them to degradative endosomal pathways. Furthermore, Nef alters cellular signalling pathways, e.g. by engaging the ζ chain of the T cell receptor. In addition, a particular proline-rich motif allows Nef to interact with several tyrosine as well as serine/threonine kinases. All of these functions correlate with effects that could indirectly favour the dissemination of the virus within the host. In fact, a diminished CD4 exposition could enhance the efficiency of infectious HIV release. Decreased amounts of exposed MHC class I molecules should lead to an impaired immunological response, mainly in terms of both anti-HIV cytotoxic T lymphocyte activity and natural killer activity. Similarly, alterations in T cell receptor signalling could induce anergy in the infected host (Bell et al, J. Gen. Vir. 1998, 79:2717-2727 and Xu et al, J. Exp. Med. 1999, 189: 1489-1496).

It has been found that humans infected with a mutant form of HIV in which Nef is deleted or mutated do not develop AIDS. Similarly it has been found that expression of F12Nef may block virus replication particularly at the level of virus assembly. The present invention makes use of such mutant Nef proteins and polynucleotides encoding therefor. Any suitable Nef mutant may be used. The wild-type Nef may be mutated using standard mutagenesis techniques. By mutagenesis we also include the deletion or substitution. In a particularly preferred embodiment site-specific mutations are introduced using the PCR overlapping technique (Taddeo (1996) Journal of Virology 70:8277-8284). Use may also be made of naturally occurring Nef mutants. The ability of Nef to impart at least some resistance or super-resistance to HIV infection may be determined by analysing viral replication. The usefulness of the Nef mutant may particularly be determined by analysing CD4 endocytosis and/or p62NAK activation as both accelerated CD4 internalization and p62NAK activation are part of the essential steps in the virus replication cycle. Such assays are known to those skilled in the art and are described in D'Aloja 2001. Alternatively a mutant HIV Nef may be reverted to wild-type and the resulting products transfected into HIV-permissible cells. Such a method would enable the identification of further useful mutations thereby enabling the identification of further mutants useful in the present invention.

In a particularly preferred embodiment use is made of the HIV-1 Nef mutant F12-HIV Nef (also F12Nef). F12Nef is characterised by three rare amino acid substitutions G140E, V153L and E177G (Carlini (1992) Journal of Virological Diseases 68:2906-2914). It has been shown that F12Nef transforms the highly productive NL4-3 HIV-1 into a replication-defective strain (Olivetta 2000 and U.S. Pat. No. 6,429,009).

In another embodiment use is made of variants of F12Nef in which the mutant HIV Nef contains one or more of the following amino acid substitutions: G140E, V153L and E177G. In one embodiment the F12Nef contains at the amino acid substitution G140E. In other embodiments the F12Nef contains at least the amino acid substitutions G140E and V153L or G140E and E177G. Such variants may be obtained by back mutating F12Nef using standard mutagenesis techniques such as the overlapping PCR technique.

When the conjugate of the present invention is in the form of a fusion protein, the F12Nef preferable forms the COOH moiety of the fusion protein.

HIV

As used herein HIV encompasses all designations assigned to those viruses implicated as causative agents of acquired immunodeficiency syndrome (AIDS) and AIDS-related complex (ARC), such as HIV, e.g. HIV-1 and HIV-2, and HTLV, e.g. HTLV-III. Of the two major HIV types, HIV-1 and HIV-2, HIV-1 is the predominant species around the world. To date, two major groups of HIV-1 exist, "M" and "O". The virus that causes the great majority of HIV-1 infections are in the M group. The O group isolates are genetically quite distant from the M group. HIV-1 subtypes of the M group include subtypes A-J.

Polynucleotides

Polynucleotides used in the invention may comprise DNA or RNA. They may be single-stranded or double-stranded. It will be understood by a skilled person that numerous different polynucleotides can encode the same polypeptide as a result of the degeneracy of the genetic code. In addition, it is to be understood that skilled persons may, using routine techniques, make nucleotide substitutions that do not affect the polypeptide sequence encoded by the polynucleotides used in the invention to reflect the codon usage of any particular host organism in which the polypeptides are to be expressed. The polynucleotides may be modified by any method available in the art. Such modifications may be carried out in order to enhance the in vivo activity or life span of polynucleotides of the invention.

Polynucleotides such as DNA polynucleotides may be produced recombinantly, synthetically, or by any means available to those of skill in the art. They may also be cloned by standard techniques.

Longer polynucleotides will generally be produced using recombinant means, for example using PCR (polymerase chain reaction) cloning techniques. This will involve making a pair of primers (e.g. of about 15 to 30 nucleotides) flanking a region of the lipid targeting sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Protein

As used herein, the term "protein" includes single-chain polypeptide molecules as well as multiple-polypeptide complexes where individual constituent polypeptides are linked by covalent or non-covalent means. As used herein, the terms "polypeptide" and "peptide" refer to a polymer in which the monomers are amino acids and are joined together through peptide or disulfide bonds. The terms subunit and domain may also refer to polypeptides and peptides having biological function.

Variants, Derivatives, Analogues, Homologues and Fragments

In addition to the specific proteins and nucleotides mentioned herein, the present invention also encompasses the use of variants, derivatives, analogues, homologues and fragments thereof.

In the context of the present invention, a variant of any given sequence is a sequence in which the specific sequence of residues (whether amino acid or nucleic acid residues) has been modified in such a manner that the polypeptide or polynucleotide in question retains at least one of its endogenous functions. A variant sequence can be modified by addition, deletion, substitution modification replacement and/or variation of at least one residue present in the naturally-occurring protein.

The term "derivative" as used herein, in relation to proteins or polypeptides of the present invention includes any substitution of, variation of, modification of, replacement of, deletion of and/or addition of one (or more) amino acid residues from or to the sequence providing that the resultant protein or polypeptide retains at least one of its endogenous functions.

The term "analogue" as used herein, in relation to polypeptides or polynucleotides includes any mimetic, that is, a chemical compound that possesses at least one of the endogenous functions of the polypeptides or polynucleotides which it mimics. Typically, amino acid substitutions may be made, for example from 1, 2 or 3 to 10 or 20 substitutions provided that the modified sequence retains the required activity or ability. Amino acid substitutions may include the use of non-naturally occurring analogues.

Proteins of use in the present invention may also have deletions, insertions or substitutions of amino acid residues which produce a silent change and result in a functionally equivalent protein. Deliberate amino acid substitutions may be made on the basis of similarity in polarity, charge, solubility, hydrophobicity, hydrophilicity, and/or the amphipathic nature of the residues as long as the transport or modulation function is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
|---|---|---|
|  |  | I L V |
|  | Polar - uncharged | C S T M |
|  |  | N Q |
|  | Polar - charged | D E |
|  |  | K R |
| AROMATIC |  | H F W Y |

"Fragments" are also variants and the term typically refers to a selected region of the polypeptide or polynucleotide that is of interest either functionally or, for example, in an assay. "Fragment" thus refers to an amino acid or nucleic acid sequence that is a portion of a full-length polypeptide or polynucleotide.

Such variants may be prepared using standard recombinant DNA techniques such as site-directed mutagenesis. Where insertions are to be made, synthetic DNA encoding the insertion together with 5' and 3' flanking regions corresponding to the naturally-occurring sequence either side of the insertion site. The flanking regions will contain convenient restriction sites corresponding to sites in the naturally-occurring sequence so that the sequence may be cut with the appropriate enzyme(s) and the synthetic DNA ligated into the cut. The DNA is then expressed in accordance with the invention to make the encoded protein. These methods are only illustrative of the numerous standard techniques known in the art for manipulation of DNA sequences and other known techniques may also be used.

Polynucleotide variants will preferably comprise codon optimised sequences. Codon optimisation is known in the art as a method of enhancing RNA stability and therefor gene expression. The redundancy of the genetic code means that several different codons may encode the same amino-acid. For example, Leucine, Arginine and Serine are each encoded by six different codons. Different organisms show preferences in their use of the different codons. Viruses such as HIV, for instance, use a large number of rare codons. By changing a nucleotide sequence such that rare codons are replaced by the corresponding commonly used mammalian codons, increased expression of the sequences in mammalian target cells can be achieved. Codon usage tables are known in the art for mammalian cells, as well as for a variety of other organisms. Preferably, at least part of the sequence is codon optimised. Even more preferably, the sequence is codon optimised in its entirety.

Vectors

As it is well known in the art, a vector is a tool that allows or facilitates the transfer of an entity from one environment to another. In accordance with the present invention, and by way of example, some vectors used in recombinant DNA techniques allow entities, such as a segment of DNA (such as a heterologous DNA segment, such as a heterologous cDNA segment), to be transferred into a host and/or a target cell for the purpose of replicating the vectors comprising the nucleotide sequences used in the invention and/or expressing the proteins used in the invention. Examples of vectors used in recombinant DNA techniques include but are not limited to plasmids, chromosomes, artificial chromosomes or viruses.

Polynucleotides used in the invention are preferably incorporated into a vector. Preferably, a polynucleotide in a vector for use in the invention is operably linked to a control sequence that is capable of providing for the expression of the coding sequence by the host cell, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under conditions compatible with the control sequences.

The control sequences may be modified, for example by the addition of further transcriptional regulatory elements to make the level of transcription directed by the control sequences more responsive to transcriptional modulators.

Vectors may be transformed or transfected into a suitable host to provide for expression of CD4 for use in present the invention. This process may comprise culturing a host cell transformed with an expression vector as described above under conditions to provide for expression by the vector of a coding sequence encoding the protein, and optionally recovering the expressed protein.

The vectors used in the present invention may be for example, plasmid or virus vectors provided with an origin of replication, optionally a promoter for the expression of a polynucleotide and optionally a regulator of the promoter. The vectors may contain one or more selectable marker genes, and/or a traceable marker such as GFP. Vectors may be used, for example, to transfect or transform a host cell.

Control sequences operably linked to sequences encoding proteins for use in the invention include promoters/enhancers and other expression regulation signals. These control sequences may be selected to be compatible with the host cell for which the expression vector is designed to be used in. The term "promoter" is well-known in the art and encompasses nucleic acid regions ranging in size and complexity from minimal promoters to promoters including upstream elements and enhancers.

The promoter is typically selected from promoters which are functional in mammalian cells, although prokaryotic promoters and promoters functional in other eukaryotic cells may be used. The promoter is typically derived from promoter sequences of viral or eukaryotic genes. For example, it may be a promoter derived from the genome of a cell in which expression is to occur. With respect to eukaryotic promoters, they may be promoters that function in a ubiquitous manner (such as promoters of a-actin, b-actin, tubulin) or, alternatively, a tissue-specific manner (such as promoters of the genes for pyruvate kinase). Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the heterologous gene can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above.

The vector used in the present invention may be a retrovirus based vector which has been genetically engineered so that it can not replicate and produce progeny infectious virus particles once the virus has entered the target cell. There are many retroviruses that are widely used for delivery of genes both in tissue culture conditions and in living organisms. Examples include and are not limited to murine leukemia virus (MLV), human immunodeficiency virus (HIV-1), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses. A detailed list of retroviruses may be found in Coffin et al., 1997, "retroviruses", Cold Spring Harbour Laboratory Press Eds: J M Coffin, S M Hughes, H E Varmus pp 758-763.

Host cells comprising polynucleotides of the invention may be used to express proteins of the invention. Host cells may be cultured under suitable conditions which allow expression of the proteins of the invention. Expression of the proteins of the invention may be constitutive such that they are continually produced, or inducible, requiring a stimulus to initiate expression.

Proteins of the invention can be extracted from host cells by a variety of techniques known in the art, including enzymatic, chemical and/or osmotic lysis and physical disruption.

Retroviruses

The retroviral vector of the present invention may be derived from or may be derivable from any suitable retrovirus. A large number of different retroviruses have been identified. Examples include: murine leukemia virus (MLV), human immunodeficiency virus (HIV), simian immunodeficiency virus, human T-cell leukemia virus (HTLV). equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV). A detailed list of retroviruses may be found in Coffin et al., 1997, "Retroviruses", Cold Spring Harbour Laboratory Press Eds: J M Coffin, S M Hughes, H E Varmus pp 758-763.

Details on the genomic structure of some retroviruses may be found in the art. By way of example, details on HIV and Mo-MLV may be found from the NCBI Genbank (Genome Accession Nos. AF033819 and AF033811, respectively). Retroviruses may be broadly divided into two categories: namely, "simple" and "complex". Retroviruses may even be further divided into seven groups. Five of these groups represent retroviruses with oncogenic potential. The remaining two groups are the lentiviruses and the spumaviruses. A review of these retroviruses is presented in Coffin et al., 1997 (ibid).

The lentivirus group can be split even further into "primate" and "non-primate". Examples of primate lentiviruses include human immunodeficiency virus (HIV), the causative agent of human auto-immunodeficiency syndrome (AIDS), and simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

A distinction between the lentivirus family and other types of retroviruses is that lentiviruses have the capability to infect both dividing and non-dividing cells. In contrast, other retroviruses—such as MLV—are unable to infect non-dividing cells such as those that make up, for example, muscle, brain, lung and liver tissue.

Even if the infection of non dividing cells is a peculiar feature of lentivirus vectors, specific conditions may be provided for a both stable and efficient transduction. These include the expression of HIV-1 Vpr (Subbramanian et al., 1998; Vodicka et al., 1998), the presence of sequences from the HIV-1 pol polypurine tract (PPT) (Follenzi et al., 2000), and the activation state of monocyte/macrophages cultures (Re and Luban, 1997).

A significant reduction in the constitutive expression of vectors may be achieved by desensitizing them to the TNFα stimulation, for instance by deleting/mutating the TNFα responsive sequences (i.e. NF-KB binding sites) in the vector HIV-1 LTR promoter.

A more direct dependence on HIV-1 expression may also be accomplished by designing a vector whose transcripts undergo nuclear retention and degradation in the absence of the Rev/RRE interaction (Emerman et al., 1989; Malim et al., 1989). Furthermore, as already described for retrovirus vectors (Grignani et al., 1998), the use of a new generation of lentivirus vectors able to express the transgene without integrating the host genome could be of a valuable importance from a biosafety point of view.

Each retroviral genome comprises genes called gag, pol and env which code for virion proteins and enzymes. In the provirus, these genes are flanked at both ends by regions called long terminal repeats (LTRs). The LTRs are responsible for proviral integration, and transcription. LTRs also serve as enhancer-promoter sequences and can control the expression of the viral genes. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5' end of the RNA. The sizes of the three elements can vary considerably among different retroviruses.

The basic molecular organisation of an infectious retroviral RNA genome is (5') R-U5-gag, pol, env-U3-R (3'). In a defective retroviral vector genome gag, pol and env may be absent or not functional. The R regions at both ends of the RNA are repeated sequences. U5 and U3 represent unique sequences at the 5' and 3' ends of the RNA genome respectively.

Host range and tissue tropism varies between different retroviruses. In some cases, this specificity may restrict the transduction potential of a recombinant retroviral vector. For this reason, many gene therapy experiments have used MLV. A particular MLV that has an envelope protein called 4070A is known as an amphotropic virus, and this can also infect human cells because its envelope protein "docks" with a phosphate transport protein that is conserved between man and mouse.

This transporter is ubiquitous and so these viruses are capable of infecting many cell types.

In some cases however, it may be beneficial, especially from a safety point of view, to target specifically restricted cells. Replacement of the env gene with a heterologous env gene is an example of a technique or strategy used to target specifically certain cell types. This technique is called pseudotyping.

The term "recombinant retroviral vector" (RRV) refers to a vector with sufficient retroviral genetic information to allow packaging of an RNA genome, in the presence of packaging components, into a viral particle capable of infecting a target cell. Infection of the target cell includes reverse transcription and integration into the target cell genome. The RRV in use typically carries non-viral coding sequences which are to be delivered by the vector to the target cell. An RRV is incapable of independent replication to produce infectious retroviral particles within the final target cell.

In a typical recombinant retroviral vector for use in gene therapy, at least part of one or more of the gag, pol and env protein coding regions essential for replication may be removed from the virus. This makes the retroviral vector replication-defective. The removed portions may then be replaced by the polynucleotide of the present invention to generate a virus capable of integrating its genome into a host genome but wherein the modified viral genome is unable to propagate itself due to a lack of structural proteins. When integrated in the host genome, expression of the polynucleotide occurs—resulting in, for example, a therapeutic and/or a diagnostic effect. Thus, the transfer of a polynucleotide into a site of interest is typically achieved by: integrating the polynucleotide into the recombinant viral vector; packaging the modified viral vector into a virion coat; and allowing transduction of a target cell.

Replication-defective retroviral vectors are typically propagated, for example to prepare suitable titres of the retroviral vector for subsequent transduction, by using a combination of a packaging or helper cell line and the recombinant vector. That is to say, that the three packaging proteins can be provided in trans.

A "packaging cell line" contains one or more of the retroviral gag, pol and env genes. The packaging cell line produces the proteins required for packaging retroviral DNA but it cannot bring about encapsidation due to the lack of apsi region. However, when a recombinant vector carrying a polynucleotide and a psi region is introduced into the packaging cell line, the helper proteins can package the psi-positive recombinant vector to produce the recombinant virus stock. This virus stock can be used to transduce cells to introduce the polynucleotide into the genome of the target cells.

The recombinant virus whose genome lacks all genes required to make viral proteins can tranduce only once and cannot propagate. These viral vectors which are only capable of a single round of transduction of target cells are known as replication defective vectors. Hence, the polynucleotide is introduced into the host/target cell genome without the generation of potentially harmful retrovirus. A summary of the available packaging lines is presented in Coffin et al., 1997 (ibid).

Retroviral packaging cell lines in which the gag, pol and env viral coding regions are carried on separate expression plasmids that are independently transfected into a packaging cell line are preferably used. This strategy, sometimes referred to as the three plasmid transfection method (Soneoka et al., 1995, Nucl. Acids Res. 23: 628-633), reduces the potential for production of a replication-competent virus since three recombinant events are required for wild type viral production. As recombination is greatly facilitated by homology, reducing or eliminating homology between the genomes of the vector and the helper can also be used to reduce the problem of replication-competent helper virus production.

An alternative to stably transfected packaging cell lines is to use transient transfected cell lines. Transient transfections may advantageously be used to measure levels of vector production when vectors are being developed. In this regard, transient transfection avoids the longer time required to generate stable vector-producing cell lines and may also be used if the vector or retroviral packaging components are toxic to cells. Components typically used to generate retroviral vectors include a plasmid encoding the gag/pol proteins, a plasmid encoding the env protein and a plasmid containing the polynucleotide. Vector production involves transient transfection of one or more of these components into cells containing the other required components.

One approach to control expression of a cDNA encoding the conjugate of the present invention involves the use of the retroviral 5' LTR. The polynucleotide sequence may also be operably linked to an internal heterologous promoter. This arrangement permits more flexibility in promoter selection. Additional polynucleotides can still be expressed from the 5'LTR or the LTR can be mutated to prevent expression following infection of a target cell.

In one embodiment the polynucleotide is inserted together with regulatory control elements in the reverse orientation to the 5'LTR to avoid any transcriptional interference.

The polynucleotide of the present invention includes a selectable marker. This strategy has an advantage for gene therapy in that a single protein is expressed in the ultimate target cells and possible toxicity or antigenicity of a selectable marker is avoided.

Delivery Systems

The invention further provides a delivery system for a conjugate of the present invention.

The delivery system of the present invention may be a viral or non-viral delivery system. Non-viral delivery mechanisms include but are not limited to lipid mediated transfection, liposomes, immunoliposomes, lipofectin, cationic facial amphiphiles (CFAs) and combinations thereof. As previously indicated when the conjugate is delivered in the form of a polynucleotide to a cell for subsequent expression therein the conjugate is preferably delivered via a retroviral vector delivery system. However, the polynucleotide may be delivered to the target cell population by any suitable Gene Delivery Vehicle, GDV. This includes but is not restricted to, DNA, formulated in lipid or protein complexes or administered as naked DNA via injection or biolistic delivery, and viruses such as retroviruses. Alternatively, the polynucleotides are delivered by cells such as monocytes, macrophages, lymphocytes or hematopoietic stem cells. In particular a cell-dependent delivery system is used. In this system the polynucleotides encoding the conjugate are introduced into one or more cells ex vivo and then introduced into the patient.

The conjugates of the present invention may be administered alone but will generally be administered as a pharmaceutical composition.

Treatment

The present invention relates to the treatment of HIV infection or related conditions. It is to be appreciated that all references herein to treatment include curative, palliative and prophylactic treatment of HIV related diseases. The treatment of mammals is particularly preferred. Both human and veterinary treatments are within the scope of the present invention.

Thus, the present invention can be used to effect intracellular immunisation so as to prevent, or at least substantially inhibit, initial HIV infection in an individual at risk from such an infection. It can also be used in the therapeutic treatment of an HIV positive patient by blocking, or at least slowing the spread of the infection, and preventing or at least delaying the onset of AIDS or ARC.

In a particularly preferred embodiment of the present invention, there is provided a method for imparting resistance to HIV infection or superinfection comprising removing an HIV-permissible cell from a patient, contacting the cell with the conjugate of the present invention so as to achieve integration and expression of the LNGFR/mutant HIV Nef and reintroducing the cell into a patient. Such ex vivo methods are described in Ferrari et al (1991) Science 251:1363. Alternatively the conjugate may be delivered to a cell in vivo.

Integration of the conjugate into nuclear genomes of cells can be monitored using, e.g. PCR in conjunction with sequencing or Southern hybridisations.

Pharmaceutical Compositions

A pharmaceutical composition is a composition that comprises or consists of a therapeutically effective amount of a pharmaceutically active agent. It preferably includes a pharmaceutically acceptable carrier, diluent or excipients (including combinations thereof). Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Examples of pharmaceutically acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

There may be different composition/formulation requirements dependent on the different delivery systems. By way of example, the pharmaceutical composition of the present invention may be formulated to be delivered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be delivered by both routes.

Typically, each conjugate may be administered at a dose of from 0.01 to 30 mg/kg body weight, preferably from 0.1 to 10 mg/kg, more preferably from 0.1 to 1 mg/kg body weight.

Polynucleotides/vectors encoding polypeptide components for use in affecting viral infections may be administered directly as a naked nucleic acid construct, preferably further comprising flanking sequences homologous to the host cell genome. When the polynucleotides/vectors are administered as a naked nucleic acid, the amount of nucleic acid administered may typically be in the range of from 1 μg to 10 mg, preferably from 100 μg to 1 mg.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example lipofectam™ and transfectam™). Typically, nucleic acid constructs are mixed with the transfection agent to produce a composition.

The composition of the present invention may also be used in conjunction with other antiretroviral drugs, in particular anti-HIV treatments such as AZT and ddI.

The routes of administration and dosages described are intended only as a guide since a skilled practitioner will be able to determine readily the optimum route of administration and dosage for any particular patient and condition.

EXAMPLE

The present invention will now be further described with reference to the following non-limiting Examples.

Example 1

Molecular Constructs

The open reading frame codifying for the ΔLNGFR/F12Nef fusion protein was obtained through the overlapping polymerase chain reaction (PCR) procedure. ΔLNGFR and F12nef genes were amplified by PCR as previously described (D'Aloja et al., 1998) from, respectively, the pUc19ΔLNGFR (Mavilio et al., 1994) and the pUc19F12-HIV (Federico et al., 1995) molecular clones, by using the DyNAzime Ext Taq polymerase (Finnzymes, Finland). Sequences of oligoprimers used are the following: ΔLNGFR Forward: 5' TTA GGATCC AAA GCG GAC CGA GCT GGA 3' (SEQ ID NO: 10); ΔLNGFR Reverse: 5' GCCACCCATGAGGATTCCCCTGTT CCA CCT CTT GAA 3' (SEQ ID NO: 11); F12nef Forward: 5' AACAGGGGAATCCTCATGGGTGGC AAG TGG TCA AAA 3' (SEQ ID NO: 12); F12nef Reverse: 5' CTC GTCGAC TCA GCA GTT TT GAA GTA CTA 3' (SEQ ID NO: 13). Both cloning restriction sites (i.e. Bam HI and Sal I, respectively) and complementary sequences are underscored. Of note, in the ΔLNGFR sequence the stop codon was replaced by the ATG initiator codon for F12nef. PCR products were purified from agarose gel, and mixed in a single PCR amplification (100 ng each in 50 μL of final volume of reaction) by using exclusively the forward ΔLNGFR and reverse F12nef oligoprimers. The final PCR product was purified, Bam HI/Sal I doubly digested, and inserted in the Bam HI and Xho I sites of the pHRprime lentivirus vector (Naldini et al., 1996).

Lentivirus vector expressing the ΔLNGFR alone was obtained through the amplification of the pUc19ΔLNGFR plasmid by using the above described forward oligoprimer, and the following reverse primer carrying an Xho I site, and retaining the stop codon: 5' AGT CTCGAG ACT CTA GAG GAT TCC CCT GTT CCA 3' (SEQ ID NO: 14). The PCR product was purified, Bam HI/Xho I doubly digested, and inserted in the homologous sites of the pHRprime lentivirus vector.

All PCR products were sequenced by the dideoxy chain termination method through the Sequenase II kit (U.S. Biochemicals, Cleveland, Ohio).

The pCMVΔR8.74 plasmid (Dull et al., 1998) was utilized as the packaging construct. The Vesicular Stomatitis Virus glycoprotein (VSV-G) (Burns et al., 1993) was expressed by an immediate-early cytomegalovirus (CMV) promoted construct.

Example 2

Cell Cultures and Immunomagnetic Selections 293 cells were grown in Dulbecco modified minimum essential medium supplemented with 10% of heat-inactivated fetal calf serum (FCS). HelaCD4/Tat (D'Aloja et al., 1998) were grown in the same medium in the presence of 0.1 mg/mL of both G418 (70% activity, Gibco-BRL, Gaithersburg, Md.), and hygromycin B (Roche, Nutley, N.J.). CEMss cells and derivative thereof were maintained in RPMI 1640 medium (Life Technologies, Gaithersburg, Md.) supplemented with 10% decomplemented FCS. Both the human recombinant Tumor Necrosis Factor (TNF)α and the neutralizing rabbit anti human TNFα purified IgG were from Peprotech (London, UK). Peripheral blood mononuclear cells (PBMC) were isolated from the buffy coat obtained from 20- to 40- years old healthy male blood donors. Peripheral blood lymphocytes (PBLs) were recovered from the supernatants of PBMC after 1 hr adherence, activated with 0.5 μg/mL of phytohaemagglutinin (PHA, Sigma Aldrich, S. Louis, Mo.), and cultivated in the presence of 100 units/mL of interleukin-2 (Roche). Monocytes were isolated by means of 1 hr adherence of PBMC, followed by immunodepletion carried out by using anti CD2, -CD3, and -CD 19 monoclonal antibodies (mAbs) (Dako, Glostrup, Denmark) coupled, in a second incubation step, with anti mouse IgG dynabeads (Dynal, Oslo, Norway). Monocytes were cultured in 48 well plates in RPMI 1640 supplemented with 20% heat-inactivated FCS.

Purity of recovered cell populations was assayed by fluorescence-activated cell sorter (FACS) (Becton Dickinson, Mountain View, Calif.) analysis. Cell preparations staining below 95% positive for CD3 or CD14 cell surface markers (specific for, respectively, lymphocytes and monocyte-macrophages) were discarded.

Both CEMss and PBLs stably expressing ΔLNGFR based vectors were isolated through the incubation for 1 hr at 4° C. with a 1:100 dilution of anti LNGFR mAb (Mavilio et al., 1994), followed by a similar incubation in the presence of anti mouse IgG Abs coupled with magnetic microbeads (Miltenyi Biotec, Auburn, Calif.), and selection by means of a magnetic device.

Example 3

Virus Preparations and Infections

Preparations of the T-cell laboratory adapted (TCLA) full length (Adachi et al., 1986) and Δnef (Chowers et al., 1994) NL4-3, and of the M-tropic ADA HIV-1 strains (Theodore et al., 1996) were obtained as supernatants of 293 cells 48 hr after the calcium phosphate transfection (Wigler et al., 1979) of the respective molecular clones. HIV-1 clinical isolates (I-III) were obtained as supernatants of CD8 depleted PBLs from AIDS patients, 7 to 14 days after the PHA activation. They were characterized as T-tropic, CXCR4 dependent viral isolates (S. Vella, personal communication). Supernatants obtained 48 hr after the co-transfection in 293 cells of vectors expressing the Δenv NL4-3 HIV-1 molecular clone (Olivetta et al., 2000), and the VSV-G protein (molar ratio 3:1), served as source of pseudotyped HIV-1 virions.

Lentivirus vector preparations were obtained by co-transfecting 293 cells with plasmids expressing the packaging construct, the lentiviral vector, and the VSV-G receptor in a molar ratio of 5:5:1. Twenty-four hr thereafter, the medium was replaced, and, after additional 24 hr, supernatants were collected, filtered (0.45 μm pore diameter), and concentrated by ultracentrifugation as described earlier (Chelucci et al., 1995). Cells were transduced by adsorbing the lentivirus vector inoculum in a small volume for 2 hr at 37° C. with occasionally shaking. Then, cells were cultivated at the appropriated concentrations for additional 16 hr, and the transduction procedures were eventually repeated. HIV-1 infections were performed in a similar way, but invariably in a single step, and by washing out the viral inoculum 48 hr after the challenge.

Example 4

Virus Detection

Virus titrations of T-tropic NL4-3 based HIV-1 strains were performed by scoring the number of syncytia on C8166 cells five days after infection (Federico et al., 1993). Infectivity titers of supernatants containing the M-tropic ADA HIV-1 strain were evaluated by the limiting dilution method 10 days after the infection of day 7 old monocyte-derived macrophages (MDM). HIV-1 clinical isolates were titrated through the limiting dilution method (D'Aloja et al., 1998) on freshly isolated PBLs from healthy donors. VSV-G pseudotyped HIV-1 were titrated by measuring the p24 HIV-1 Gag contents through a quantitative enzyme-linked immunosorbent assay (ELISA, Abbott, North Chicago, Ill.).

The amounts of both HIV-1 and lentivirus vectors were estimated through the reverse transcriptase (RT) assay (Rossi et al., 1987), and/or the p24 HIV-1 Gag specific ELISA.

Example 5

Protein Detection

Indirect FACS analyses for the detection of cell membrane ΔLNGFR molecules were performed as previously described (Bona et al., 1997). The levels of CD4 and CD8 receptors were measured through a direct immunofluorescence analysis as already reported (Alessandrini et al., 2000), by using fluorescein isothiocyanate (FITC)-conjugated anti CD4 (Dako), and/or phycoerythrine (PE)-conjugated anti CD8 (Becton-Dickinson) mAbs. The levels of CXCR4 HIV co-receptor were measured by using the 12G5 mAb in indirect FACS analysis. All FACS analyses on monocyte/macrophage cells were performed after a Fc blocking step, carried out by incubating cells 15 min at room temperature (r.t.) with 10 μg/mL of human IgG (Dako).

Percentages of cells expressing intracytoplasmic HIV-1 Gag related products were evaluated by FACS analyses after treatment with Permeafix (Ortho Diagnostic, Raritan, N.J.) for 30 min at r.t., and labeling for 1 hr at r.t. with 1:50 dilution of KC57-RD1 PE-conjugated anti HIV-1 Gag mAb (Coulter Corp., Hialeah, Fla.). In double FACS analyses, the membrane labeling always preceded that of intracytoplasmic products.

Western blot assay was performed through the enhanced chemoluminescence (ECL) method as described (D'Aloja et al., 1998), by using a sheep anti Nef hyperimmune serum at a dilution of 1:500, and, as control, an anti human actin mAb. Both were reacted in a second step with a 1:20,000 dilution of horseradish peroxidase (HRP) conjugated protein G (Biorad Laboratories, Richmond, Calif.). The amounts of TNFα in lymphocyte cell supernatants were determined by ELISA (R&D System, Minneapolis, Minn.).

Example 6

The Lentivirus Vector Expressing the ΔLNGFR/F12Nef Fusion Protein Transduces Human Cells Efficiently The schematic maps of lentivirus vectors expressing the ΔLNGFR alone (HN vector, used throughout as control vector), or the ΔLNGFR/F12Nef fusion protein (NF vector), are depicted in FIG. 1. Each vector was separately co-transfected in 293 cells together with both the pCMVΔR8.74 packaging construct, and a CMV driven vector expressing the VSV-G protein, in a molar ratio of 5:5:1. Forty-eight hr post transfection, clarified supernatants were 200 folds concentrated by ultracentrifugation, and titrated for both p24 HIV-1 Gag contents and reverse transcriptase activity. In a representative experiment, a preparation of the HN vector was obtained containing 38 ng/μL of p24 HIV-1 Gag, with an RT activity of $2.6 \times 10^6$ cpm/μL, and a preparation of the NF vector containing 22.5 ng/μL of p24 HIV-1 Gag with an RT activity of $1.52 \times 10^6$ cpm/μL were obtained for the NF vector. These data suggested that processes underlying the assembling and release of recombinant lentivirus particles proceeded with a similar efficiency in cells producing either vector.

Figure 2:
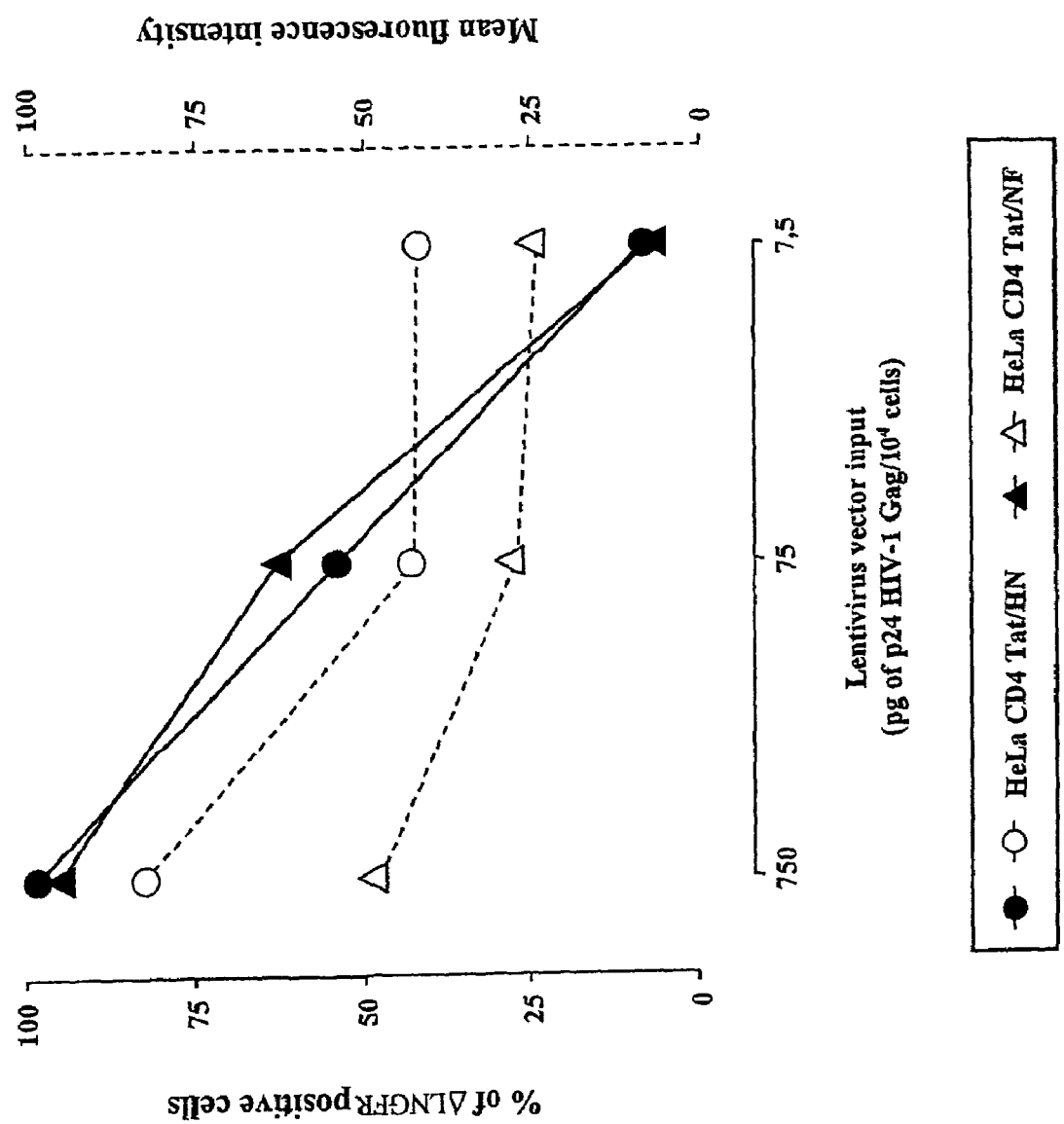
FIG. 2. is a graph showing that both HN and NF lentivirus vectors transduce human cells with a similar efficiency. HeLaCD4 cells constitutively expressing the HIV-1 Tat protein were transduced in duplicate with different doses of HN or NF vectors. After 24 hr, cell cultures were washed and, after additional 24 hr, analyzed by FACS for the expression of membrane ΔLNGFR. Both the percentages of positive cells (closed symbols), and the mean fluorescence intensity (MFI) values (means of duplicated samples, open symbols) of ΔLNGFR positive cell fractions, are reported. Data refer to a representative of two independent experiments.

The transduction efficiency of both lentivirus vector preparations was tested by infecting HeLaCD4 cells constitutively expressing the HIV-1 Tat protein (i.e., the most powerful intracellular activator of the HIV-1 LTR). HeLaCD4/Tat cells were transduced in duplicate with decreasing (i.e., from 750 to 7.5 pg of p24 HIV-1 Gag/$10^4$ cells) doses of each vector. Forty-eight hr thereafter, cells were harvested and analyzed for the ΔLNGFR membrane expression in terms of both percentages of positive cells, and mean fluorescence intensity (MFI) values (FIG. 2). The infection efficiencies of the two vectors seemed quite similar. In fact, vector amounts corresponding to 75 pg of p24 HIV-1 Gag protein/$10^4$ cells successfully infected more than 50% of HeLaCD4/Tat cells, whatever vector used. Differently, through the measurement of the MFI relative to the positive cell populations, the inventor observed a nearly two folds reduction in NF- with respect to HN- transduced cells, that is suggestive of a stronger infection and/or expression efficiency of the HN vector. Also, the reduction in the MFI detectable by lowering the vector input from 750 pg to 75 pg, should be the consequence of the entry and the expression of more than a single viral particle per cell at the highest vector inoculum.

In sum, the data demonstrated that the transducing efficiency of the NF vector was high, and comparable to that of the control vector expressing the ΔLNGFR alone.

Example 7

Both HN and NF Vectors are Targetable by HIV-1 LTR Activators

Figure 3:
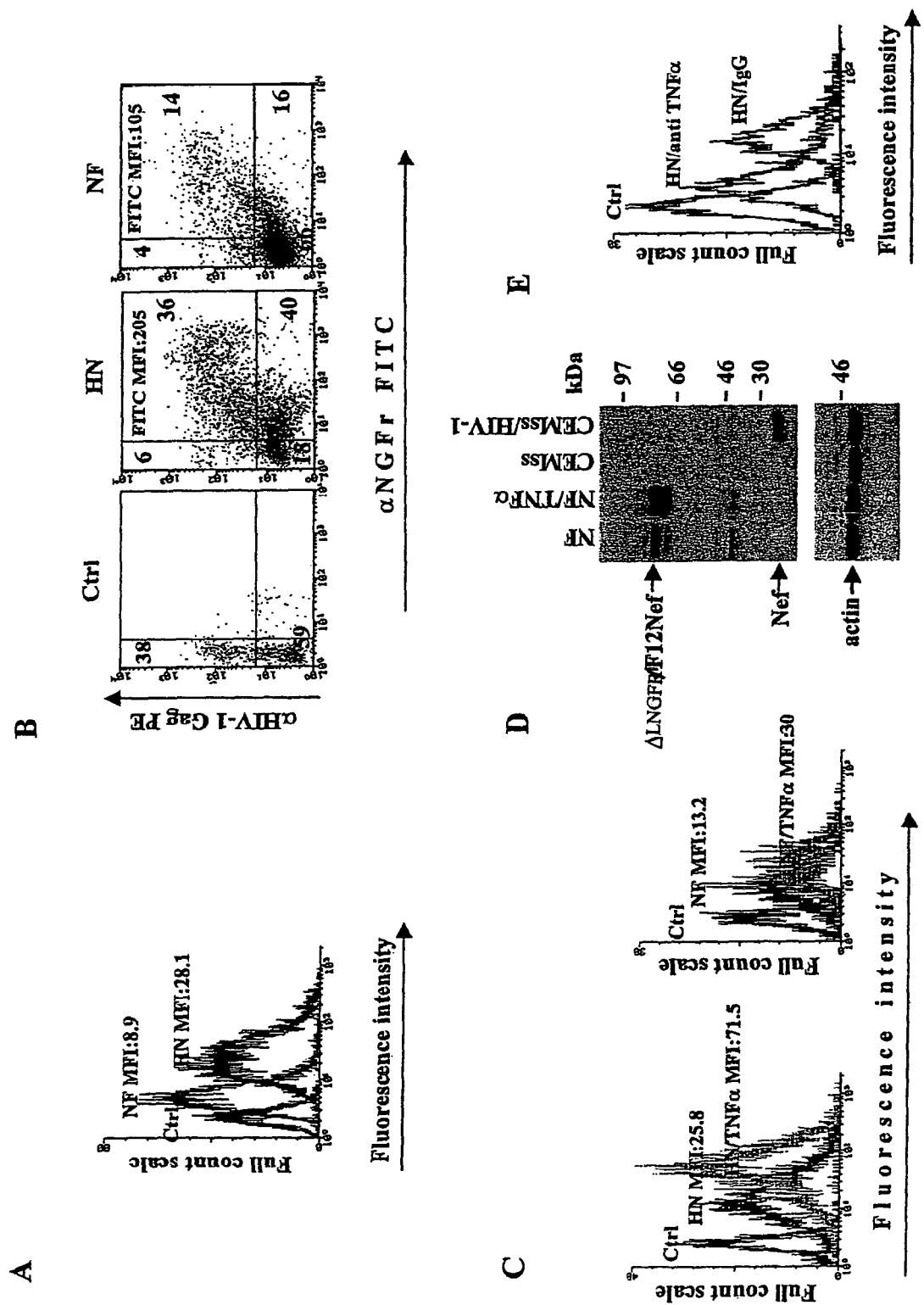
FIGS. 3A-E. show graphs illustrating that the expression of both HN and NF vectors in CEMss cells is strongly induced by HIV-1 infection and modulated by TNFα.

The expression of both HN and NF vectors depended on the HIV-1 LTR activation. This could be achieved by infecting transduced cells with HIV-1, or by treating them with soluble factors such as HIV-1 Tat (for a review, see Roebuck and Saifuddin, 1999), or TNFα (Chen et al., 1997; Duh et al., 1989). In order to analyze the inducibility of both HN and NF vectors in human cells, stably transduced cells were recovered upon infection of $2 \times 10^5$ CD4+ human lymphoblastoid CEMss cells with a dose of each vector corresponding to 10 ng of p24 HIV-1 Gag. FACS analysis performed 48 hr thereafter showed that >95% of transduced CEMss cells expressed ΔLNGFR at the cell membrane. Clearly, a basal (i.e. independent from HIV-1 expression) activity of both lentivirus vectors was detectable. After additional seven days, when the percentage of ΔLNGFR positive cells dropped to 10-20%, cells expressing the ΔLNGFR were isolated by means of an immunomagnetic based protocol. The FACS analysis for the expression of the ΔLNGFR on the selected cell populations confirmed that both vectors showed a low constitutive activation (FIG. 3A). To assess the inducibility of vectors upon HIV-1 expression, both CEMss HN and -NF cells were infected with HIV-1 at a multiplicity of infection (MOI) of 0.5. Four days thereafter, HIV-1 infected cells were analyzed for the activation of the lentivirus constructs by means of an anti HIV-1 Gag/ΔLNGFR double FACS analysis (FIG. 3B). Due to the F12Nef antiviral activity, an higher proportion of CEMss HN with respect to CEMSS NF cells appeared to express HIV-1 proteins. However, in both cases, the levels of ΔLNGFR expression directly correlated with the amounts of HIV-1 Gag products. As already noticed in uninfected cells, the HN vector expressed higher levels of the transgene with respect to NF.

Consistent results have been obtained by treating transduced cells with soluble factors activating the HIV-1 LTR. The treatment of transduced CEMss cells with 10 ng/mL of recombinant human TNFα for 16 hr led to sharp enhancements in the ΔLNGFR expression (FIG. 3C), that, however, appeared significantly lower than those detected upon HIV-1 infection. The TNFα specific induction of the ΔLNGFR/F12Nef fusion protein was also confirmed by the anti Nef Western blot analysis, where the transgene product appeared as a ≅75 kDa doublet (FIG. 3D). Taken together, these results demonstrate that both HN and NF lentivirus vectors could be efficiently targeted by HIV-1 LTR activators.

Finally, the inventor sought to identify the factor(s) involved in lentivirus vector spontaneous activity. It has been reported that human lymphoblastoid cell lines release TNFα, i.e. a potent HIV-1 LTR activator (Chen et al., 1997; Duh et al., 1989), in a range of 0.1-1 ng/mL (Jia et al., 1995; Sung et al., 1988). Hence, it was tested whether the spontaneous activity of the pHRprime based vectors was the consequence of the presence of constitutively released TNFα. CEMss HN cells were treated for 16 hr with a dose of anti TNFα Abs able to neutralize the amounts of TNFα detected in CEMss HN supernatants (i.e., 0.1-0.3 ng/mL), and the vector expression was tested by means of ΔLNGFR specific FACS analysis. The significant reduction of the ΔLNGFR specific signal upon anti TNFα Abs treatment (FIG. 3E) indicates that the spontaneous activity of the pHRprime based vectors could be at least in part due to the presence of TNFα in the supernatants of transduced CEMss cells.

Example 8

Figure 4:
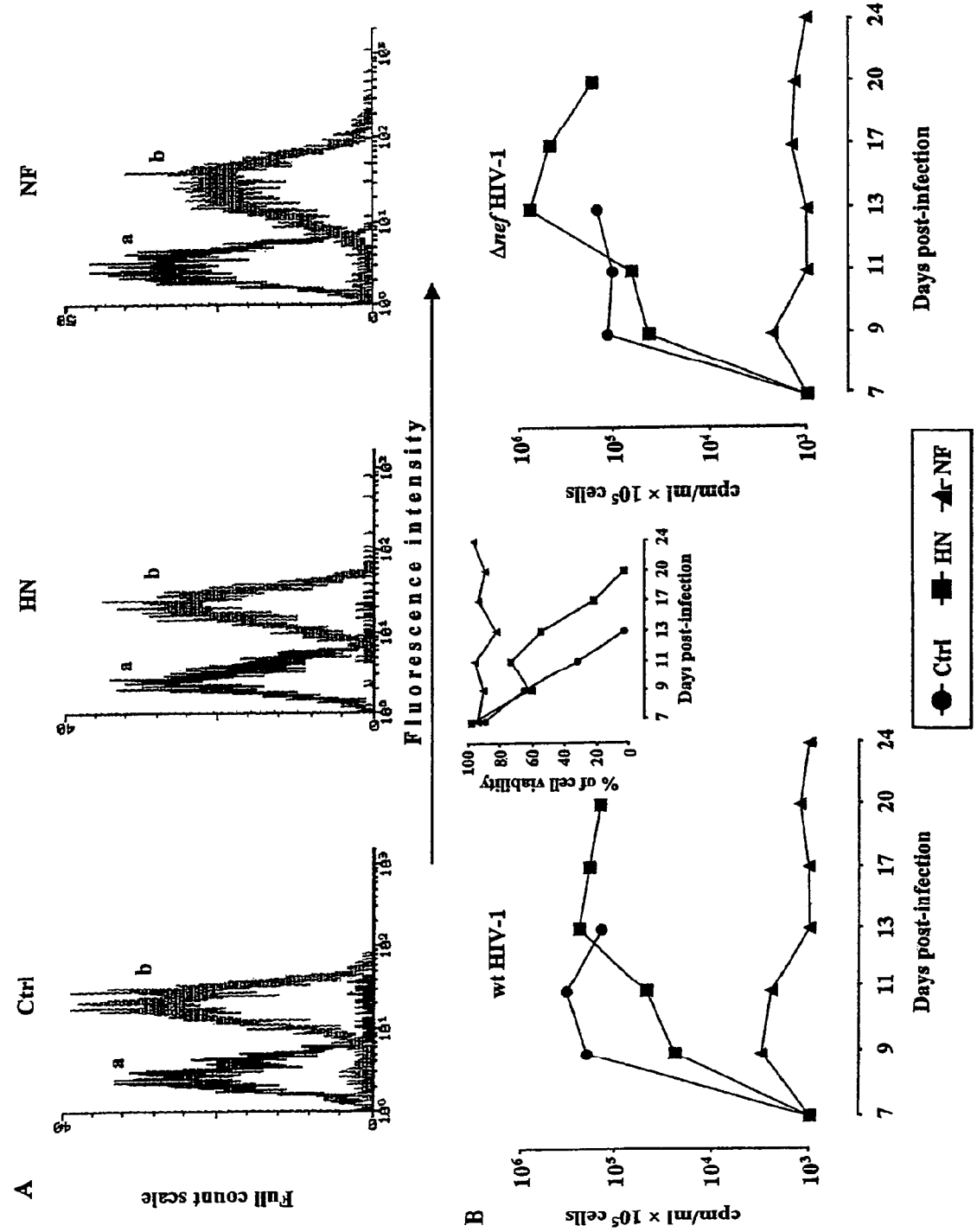
FIGS. 4A & B. show graphs illustrating that the CEMss NF transduced cell population is protected by the HIV-1 challenge in a CD4 independent manner.
(FIG. 4B) RT activities measured as counts per minute (cpm) per milliliter of supernatant normalized for $10^5$ cells after background subtraction at different days after the infection of CEMss HN or NF cells with wt or ΔnefNL4-3 HIV-1 strains (MOI 0.02). Parental CEMss cells were used as control cell population. Percentages of cell viability in cultures infected with the wt HIV-1 are reported in the insert. Cell viability of uninfected cell populations was >95% throughout the time points analyzed. Data from a representative of two independent experiments are reported.

CEMss Cells Expressing the ΔLNGFR/F12Nef Fusion Protein Resist to HIV-1 Challenge Next, the effects of ΔLNGFR/F12Nef fusion protein in terms of anti HIV-1 activity were analyzed. First, it was established that control, HN and NF CEMss cells replicated with similar doubling times. Then, it was assessed that the expression of the major HIV receptor, i.e. CD4, remained essentially unaltered in both transduced cell lines with respect to the control cells (FIG. 4A). No variations in the expression of the CXCR4 HIV co-receptor were detected as well. Transduced cell populations and, as control, parental CEMss cells were infected with either the full length or the nef deleted NL4-3 HIV-1 strains (MOI 0.02). As shown in FIG. 4B, CEMss NF cells nicely resisted to the HIV-1 challenge, independently to the expression of wild type Nef. Such a viral inhibition was also independent from the cell cycle, as no inhibition of the cell growth has been noticed in the HIV-1 infected with respect to uninfected CEMss NF cells. Conversely, the cell viability of both control and CEMss HN infected cells decreased over the time (insert of FIG. 4B), thus limiting the lag of virus detection in the supernatants. Of note, a some degree of resistance to HIV-1 replication has been detected in CEMss HN cells also, allowing infected cultures to release lower amounts of HIV-1, and/or to survive better the HIV-1 infection with respect to the parental infected cells (insert of FIG. 4B). This is consistent with previously reported results (An et al., 1999; Bukovsky et al., 1999), and was explained in terms of competition between the vector RNA and the infecting viral genome for both the incapsidation process and Tat/Rev availability.

Example 9

Figure 5:
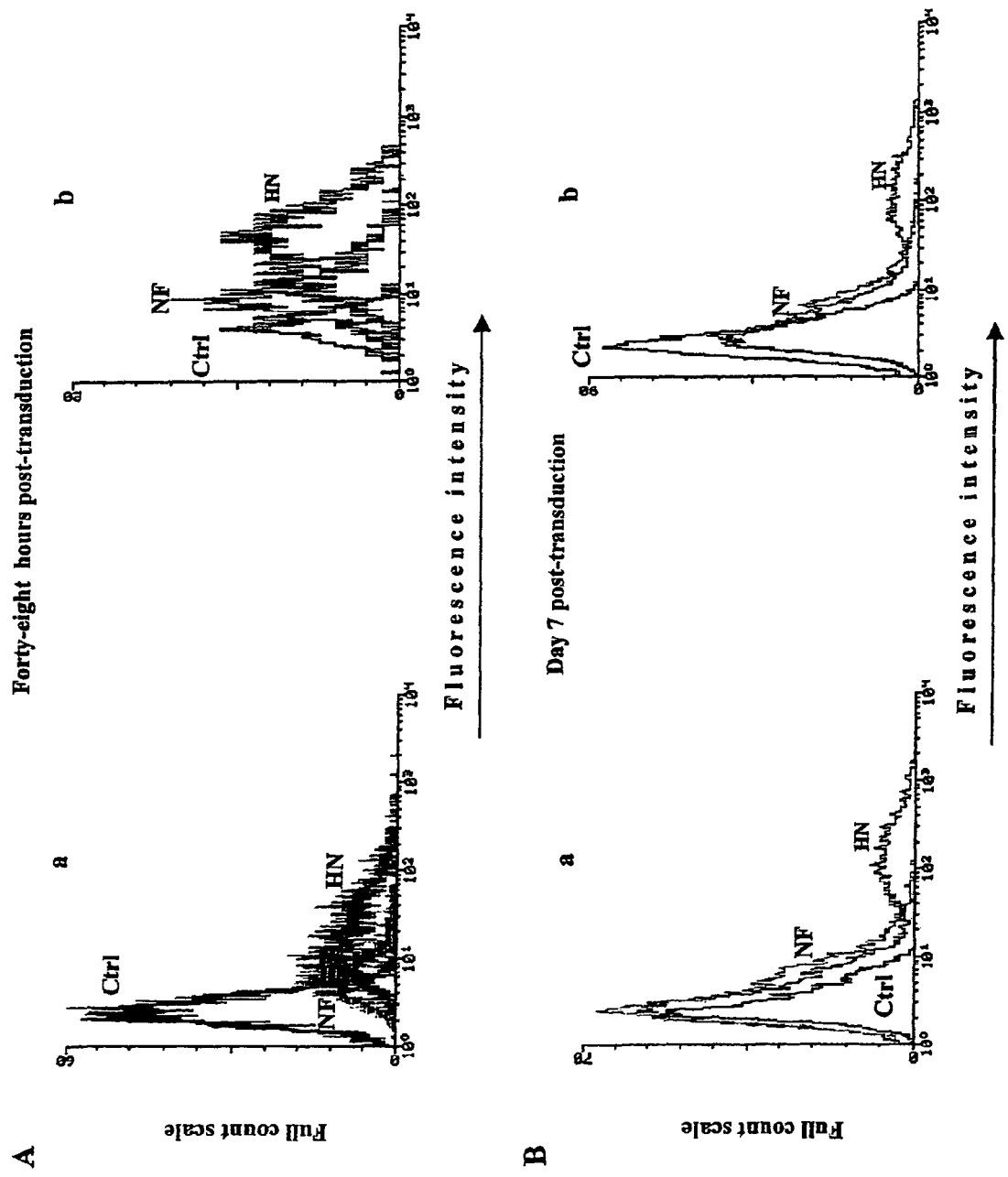
FIGS. 5A & B. show graphs illustrating that both HN and NF vectors transduce activated human PBLs efficiently.
(FIG. 5B) FACS analysis for the expression of ΔLNGFR performed 7 days after the transduction on the same PBLs populations described in panel A. As a control, non transduced PBLs from the same donors grown in parallel cultures were utilized (Ctrl). In all analyses, the MFI of both HN and NF cell populations upon labeling with species and isotype matched IgG overlapped that of anti LNGFR labeled control PBLs.
Figure 6:
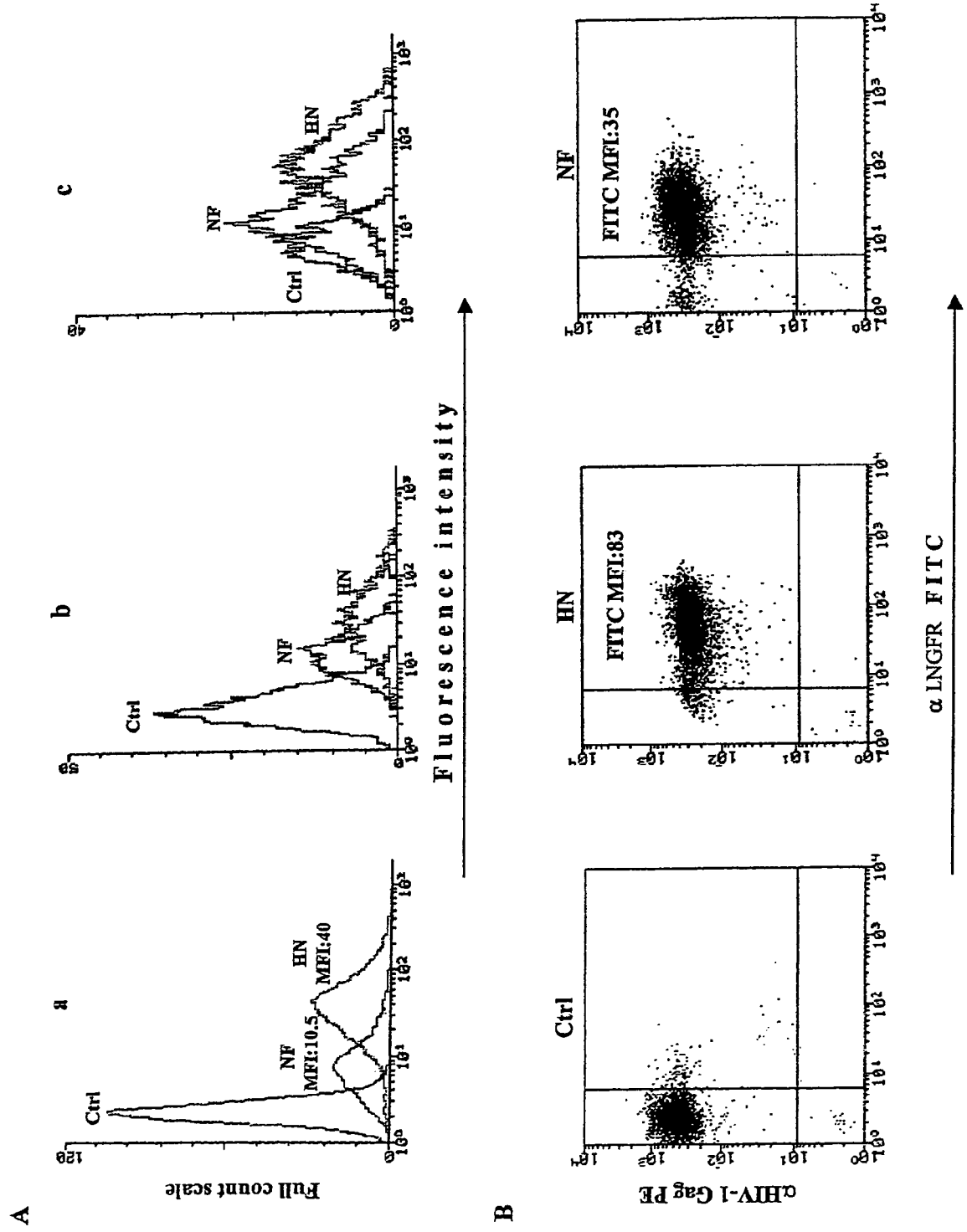
FIGS. 6A & B. show graphs illustrating the expression of both HN and NF vectors in transduced PBLs is enhanced by HIV-1 expression.
(FIG. 6B) HIV-1 Gag/ΔLNGFR double florescence FACS analysis of HN or NF stably transduced PBLs after the infection with (VSV-G) pseudotyped Δenv HIV-1. Twenty-four hr after the positive immunoselection, fractions of the PBLs from donor a, also analyzed for the basal levels of the cell membrane ΔLNGFR (panel A), were infected with 5 ng/$10^5$ cells of (VSV-G) Δenv HIV-1, and the ΔLNGFR membrane expression was evaluated 48 hr thereafter. Non transduced PBLs from the same donor were used as control (Ctrl). The MFI values for the ΔLNGFR expression in HIV-1 positive HN and NF transduced cell populations are indicated. Quadrants were set considering the fluorescence levels of double labeled uninfected parental PBLs.

PHA Stimulated Human PBLs are Efficiently Transduced by HN and NF Lentivirus Vectors Human PBLs represent the preferential target for HIV replication. Clearly, testing the actual efficiency of any anti HIV gene therapy design in PBL cell cultures is mandatory. PBLs isolated from PBMC were activated with PHA for two days. Then, they underwent two cycles of transduction through the infection with 10 ng/$10^4$ cells of each vector, and, after additional 48 hr, FACS analyses for the expression of the ΔLNGFR expression were carried out. The large majority of challenged cells appeared successfully transduced (FIG. 5A). Similarly to that detected in transduced CEMss cells, a basal activity of vectors was detectable (FIG. 5A). Again, this could be at least in part the consequence of the TNFα typically released by activated PBLs (Conlon et al., 1992; Cuturi et al., 1987; Lindstein et al., 1989; Sung et al., 1988), as the treatment with anti TNFα antibodies significantly reduced the ΔLNGFR basal expression. In order to recover stably transduced PBLs, the ΔLNGFR based immunoselection was performed after additional seven days. As expected, at this time the number of ΔLNGFR expressing cells significantly decreased (FIG. 5B), likely representing the fraction of transduced cells able to integrate the vectors stably. Transduced PBLs were tested for the ΔLNGFR expression by FACS three days after the positive immunoselection (FIG. 6A). To assay the inducibility of both HN and NF vectors upon HIV-1 expression, stably transduced PBLs were infected with 5 ng/$10^5$ cells of (VSV-G) pseudotyped Δenv HIV-1 24 hr after the selection, and analyzed for the ΔLNGFR expression after additional 48 hr. The use of pseudotyped HIV-1 allowed to maximize the infection efficiency, as demonstrated by the high levels of HIV-1 protein expression detected in virtually all challenged cells (FIG. 6B), and also to extend the analysis to CD8+ lymphocytes. Similarly to that already described for transduced CEMss cells, the HIV-1 infection led to a strong increase in the amounts of the transgene products (FIG. 6B), i.e. 2- and 3.5 for, respectively, HN and NF vectors. Notably, inhibition of the HIV-1 expression in ΔLNGFR/F12Nef expressing PBLs upon (VSV-G) HIV-1 single cycle infection was not observed, even by lowering the viral input up to 100-folds. This appeared consistent with the already reported findings demonstrating that F12Nef interferes with late steps of the HIV-1 replication (Olivetta et al., 2000; Fackler et al., 2001).

From these results, it was concluded that both HN or NF vectors stably integrated in PBLs could be efficiently targeted by HIV-1 infection.

Example 10

Figure 7:
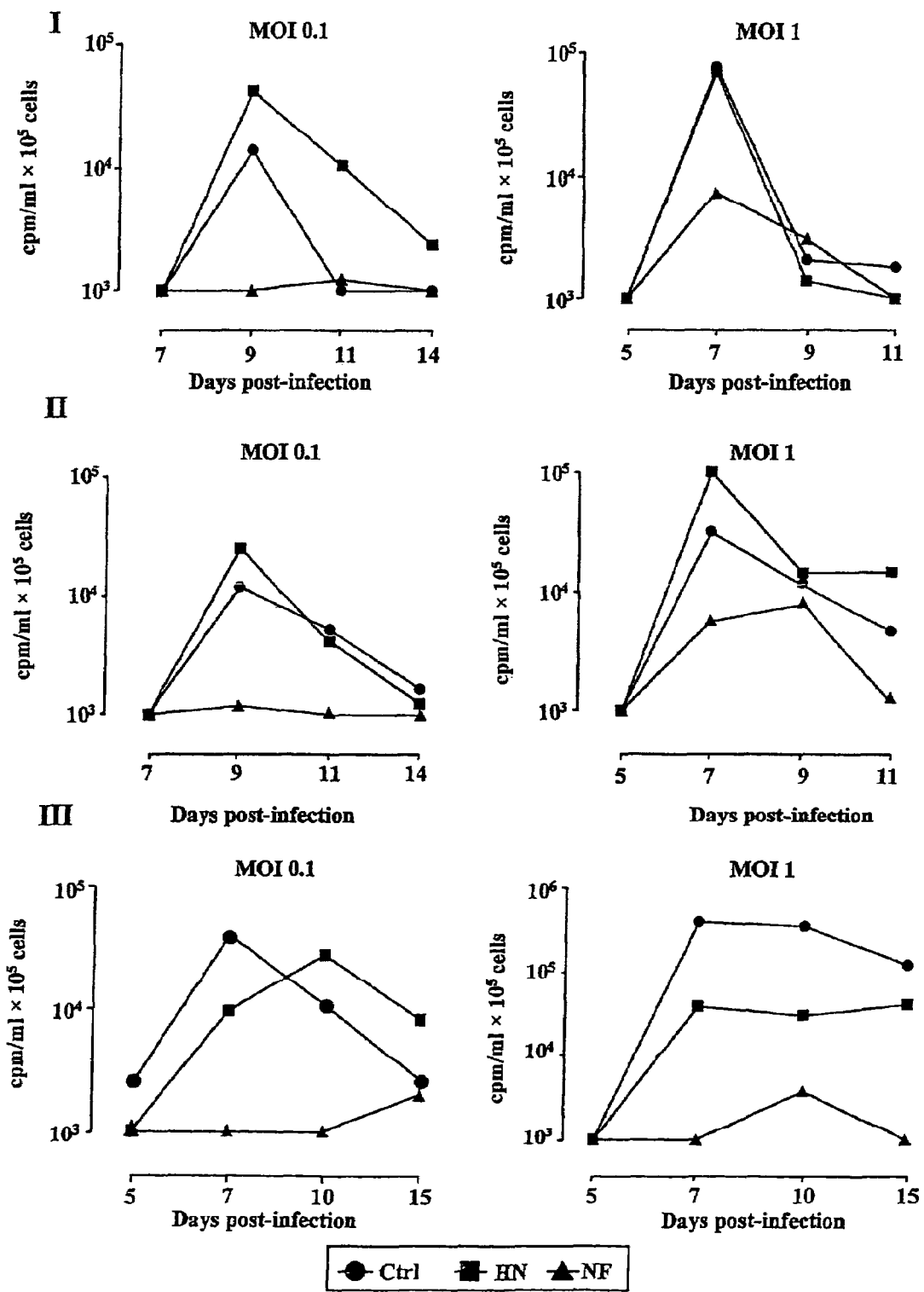
FIGS. 7I-III. show graphs illustrating that the replication of HIV-1 clinical isolates is strongly inhibited in NF transduced PBLs. RT activities measured as cpm per milliliter of supernatant normalized for $10^5$ cells after background subtraction at different days after the infection with HIV-1 of PBLs stably transduced with HN or NF vectors. Three days after the ΔLNGFR specific positive immunoselection, transduced PBLs from three different donors (a-c) were challenged each with a different T-tropic HIV-1 clinical isolate (I-III) at the indicated MOIs. Parental PBLs were used as control cells.

Human PBLs Expressing the ΔLNGFR/F12Nef Fusion Protein Resist to HIV-1 Challenge Stably transduced PBL cultures from three healthy donors (a-c, see FIG. 6) were challenged with 0.1-1 MOIs of three different T-tropic HIV-1 clinical isolates (I-III). Clearly, PBLs transduced with the NF construct were protected efficiently against HIV-1 spread (FIG. 7). Results appeared consistent among different cell populations and HIV-1 clinical isolates considered. Low amounts of HIV-1 particles have been noticed solely in the supernatants from cell cultures infected with the highest MOI, implying that the F12Nef antiviral activity should be overridden exclusively by very high, and clearly not physiological viral inputs. Alternatively, this could be the consequence of the presence of residual untransduced lymphocytes contaminating the positively immunoselected cell populations.

Figure 8:
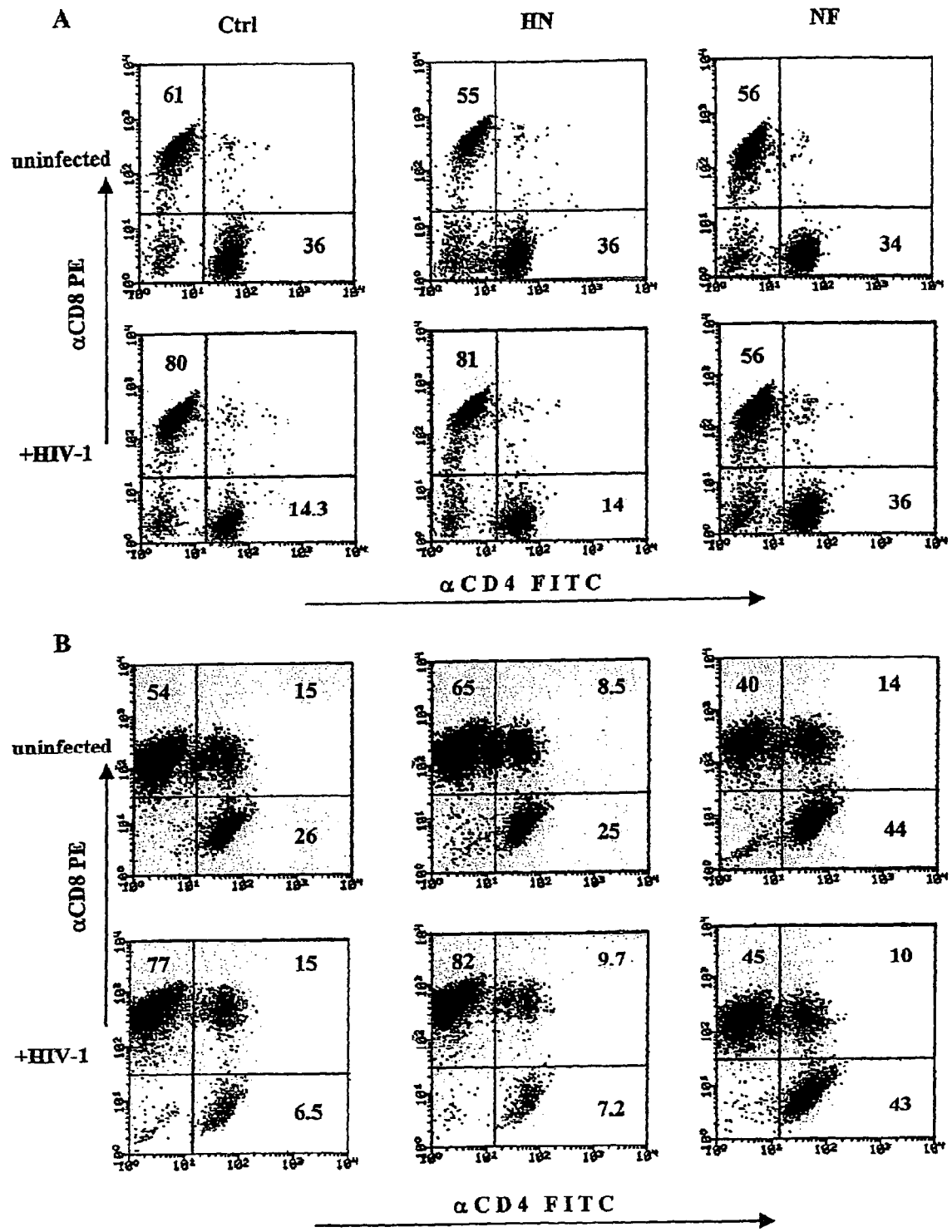
FIGS. 8A & B. show graphs illustrating that the HIV-1 challenge does not influence the CD4/CD8 cell ratio in the NF transduced PBLs. CD4/CD8 double fluorescence FACS analyses on HN and NF stably transduced PBLs ten days after the infection with two different HIV-1 clinical isolates (MOI 1). PBLs cultures infected with the HIV-1 clinical isolate I (FIG. 8A) and III (FIG. 8B) (see FIG. 7), were doubly labeled with FITC-conjugated anti CD4 and PE-conjugated anti CD8 mAbs. In parallel, analyses were carried out also in non infected cell cultures and, as control, in non transduced PBLs (Ctrl). Quadrants were set on the basis of the fluorescence levels of each PBL population after the double labeling with PE and FITC conjugated species and isotype matched IgGs. Percentages of cells scored for each quadrant are reported.

Typically, the in vivo HIV replication correlates with a progressive loss of CD4+ lymphocytes. In order to evaluate possible influences of the challenging HIV-1 on the growth of the CD4+ subpopulation of the ΔLNGFR/F12Nef expressing PBLs, control and transduced PBLs were scored for the CD4/CD8 ratio ten days after the HIV-1 challenge. Analyses reported in FIG. 8 have been performed on PBLs infected with the HIV-1 clinical isolate I (panel A), and III (panel B), MOI 1. PBLs expressing the ΔLNGFR/F12Nef fusion protein maintained a constant CD4/CD8 ratio, whereas significant reductions in the proportion of CD4+ cells were detectable in both control and HN transduced cell populations. Overlapping results were obtained by analyzing the infected cell populations al later time points. Importantly, no significant differences in the cell growth among all uninfected cell populations have been appreciated. Differently, a slight decrease ($\leq 10\%$) in the cell viability of both control and HN with respect to NF transduced PBLs has been noticed upon HIV-1 infection.

These data indicate that the block of HIV-1 spread in NF transduced cells tightly correlated with an efficient action against the cytocidal effect of HIV-1 on CD4+ PBLs.

Example 11

Figure 9:
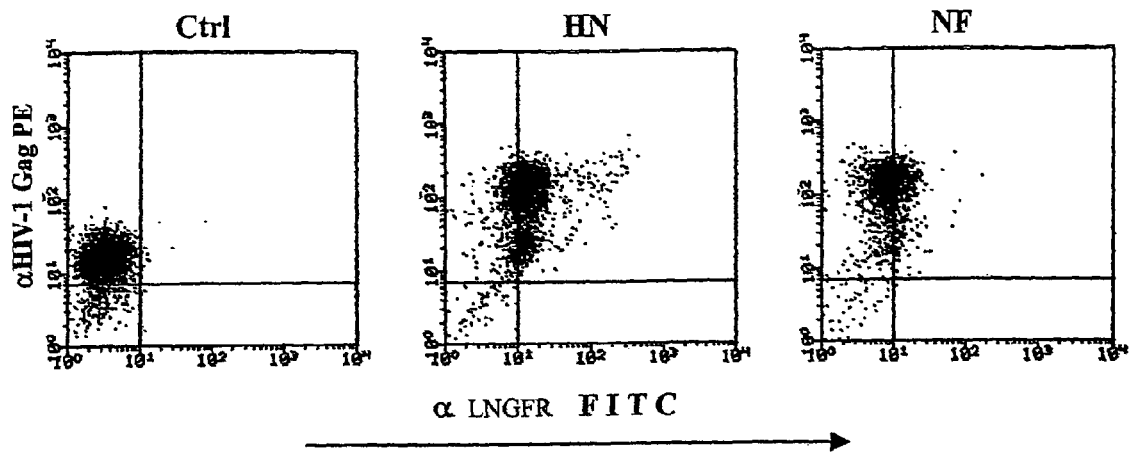
FIGS. 9A & B. show graphs illustrating that the HIV-1 replication is inhibited in NF transduced MDM. population. Data from one experiment representative of two are reported.
(FIG. 9B) HIV-1 amounts measured as pg of p24 HIV-1 Gag in the supernatants of the HN or NF transduced MDM at different days after infection with 0.5 MOI of the M-tropic ADA HIV-1 isolate. The parental MDM were used as control cell population. Data from one experiment representative of two are reported.
Figure 9:
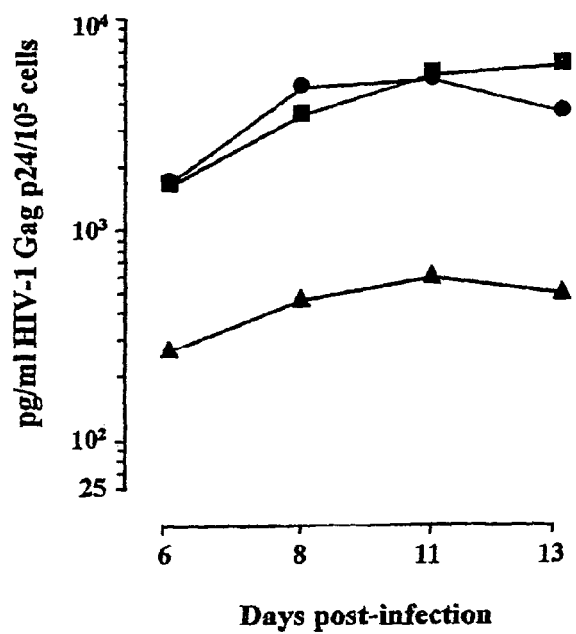

Monocyte Derived Macrophages Transduced by NF Vector are Protected from HIV-1 Infection Monocyte/macrophages (m/m) represent an attractive target for the anti HIV-1 gene therapy, as they replicate HIV-1 very efficiently both in vivo and in vitro. At least in vivo, m/m well resist to the HIV-1 cytocidal effect, thus representing a reservoir for HIV-1 infection. The inventor sought to transduce freshly isolated MDM with both HN and NF lentivirus vectors. In our hands, the currently available cell sorting techniques resulted heavily detrimental for the transduced MDM cell populations. Thus, a reliable analysis of the effects of ΔLNGFR/F12Nef fusion protein in MDM required the stably transduction of the broad majority of cells. This was achieved in two out of the seven attempts performed. MDM were cultivated in 48-well plates, and infected in replicated wells with 10 ng/$10^5$ cells of each lentivirus vector. The proportion of transduced MDM was evaluated through the infection with 5 ng/$10^5$ cells of (VSV-G) pseudotyped Δenv HIV-1 (FIG. 9A), as neither spontaneous nor TNFα induced activity of either lentivirus vector has been noticed in transduced MDM. As already detected in other cell types, the level of vector expression appeared stronger in HN than in NF transduced MDM. Of note, the infection with pseudotyped HIV-1 led both transduced MDM cell populations to express significantly higher HIV-1 Gag related products with respect to the non transduced cells (FIG. 9A). More importantly, the challenge of NF transduced MDM with the M-tropic ADA HIV-1 strain (MOI 0.5) led to a viral release significantly reduced with respect to control MDM cell populations (FIG. 9B). The viability of challenged cell populations well correlated with the HIV-1 replication extents.

Data obtained in the MDM system are in keeping with those obtained in lymphocytes.

Although the HIV-1 expression strongly increased the expression levels of the transgenes, constitutive activation of the vectors was detectable in uninfected lymphocytic cells. It was proved that such constitutive activity did not apparently influence the cell viability, and correlated, at least in part, with the presence of TNFα, a soluble factor inducing HIV-1 LTR activation (Chen et al., 1997; Duh et al., 1989), and constitutively released by both CEMss cells and activated PBLs (Conlon et al., 1992; Cuturi et al., 1987; Jia et al., 1995; Lindstein et al., 1989; Sung et al., 1988). The presence of residual ΔLNGFR expression detected after the treatment with anti TNFα neutralizing antibodies, suggested that additional soluble factor(s) and/or endogenous mechanism(s) are partly on the basis of the observed spontaneous activity. It is worthy of note that the expression of HN or NF vectors did not modulate the TNFα expression.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are apparent to those skilled in molecular biology or related fields are intended to be within the scope of the following claims.

REFERENCES

ADACHI, A., GENDELMAN, H. E., KOENIG, S., FOLKS, T., WILLEY, R., RABSON, A., and MARTIN, M. A. (1986). Production of acquired immunodeficiency syndrome-associated retrovirus in human and non human cells transfected with an infectious molecular clone. J. Virol. 59, 284-291.

AIKEN, C., KONNER, J., LANDAU, N. R., LENBURG, M. E., and TRONO, D. (1994). Nef induces CD4 endocytosis: requirement for a critical dileucine motif in the membrane-proximal CD4 cytoplasmic domain. Cell 76, 853-864.

ALESSANDRINI, L., SANTARCANGELO, A. C., OLIVETTA, E., FERRANTELLI, F., D'ALOJA, P., PUGLIESE, K., PELOSI, E., CHELUCCI, C., MATTIA, G., PESCHLE, C., VERANI, P., and FEDERICO, M. (2000). T-tropic human immunodeficiency virus (HIV) type 1 Nef protein enters human monocyte-macrophages and induces resistance to HIV replication: a possible mechanism of HIV T-tropic emergence in AIDS. J. Gen. Virol. 12, 2905-2917.

AN, D. S., MORIZONO, K., LI, Q. X., MAO, S. H., LU, S., and CHEN, I. S. (1999). An inducible human immunodeficiency virus type 1 (HIV-1) vector which effectively suppresses HIV-1 replication. J. Virol. 73, 7671-7677.

BAUR, A. S., SAWAI, E. T., DAZIN, P., FANTL, W. J., CHENG-MAYER, C., and PETERLIN, B. M. (1994). HIV-1 Nef leads to inhibition or activation of T cells depending on its intracellular localization. Immunity 1, 373-384.

BAUR, A. S., SASS, G., LAFFERT, B., WILLBOLD, D., CHENG-MAYER, C., and PETERLIN, B. M. (1997). The N-terminus of Nef from HIV-1/SIV associates with a protein complex containing Lck and a serine kinase. Immunity 6, 283-291.

BONA, R., D'ALOJA, P., OLIVETTA, E., MODESTI, A., MODICA, A., GERACI, A., FERRARI, G., VERANI, P., and FEDERICO, M. (1997). Aberrant, noninfectious HIV-1 particles are released by chronically infected human T cells transduced with a retroviral vector expressing an interfering HIV-1 variant. Gene Ther. 4, 1085-1092.

BUKOVSKY, A. A., SONG, J. P., and NALDIM, L. (1999). Interaction of human immunodeficiency virus-derived vectors with wild-type virus in transduced cells. J. Virol. 73, 7087-7092.

BURNS, J. C., FRIEDMANN, T., DRIEVER, W., BURRASCANO, M., and YEE, J. K. (1993). Vesicular stomatitis virus G glycoprotein pseudotyped retroviral vectors: concentration to very high titer and efficient gene transfer into mammalian and non mammalian cells. Proc. Natl. Acad. Sci. USA 90, 8033-8037.

CHADWICK, D. R., and LEVER, A. M. (2000). Antisense RNA sequences targeting the 5' leader packaging signal region of human immunodeficiency virus type-1 inhibits viral replication at post-transcriptional stages of the life cycle. Gene Ther. 7, 1362-1368.

CHELUCCI, C., HASSAN, H. J., LOCARDI, C., BULGARINI, D., PELOSI, E., MARIANI, G., TESTA, U., FEDERICO, M., VALTIERI, M., and PESCHLE, C. (1995). In vitro human immunodeficiency virus-1 infection of purified hematopoietic progenitors in single-cell culture. Blood 85, 1181-1187.

CHEN, B. K., FEINBERG, M. B., and BALTIMORE, D. (1997). The kappaB sites in the human immunodeficiency virus type 1 long terminal repeat enhance virus replication yet are not absolutely required for viral growth. J. Virol. 71, 5495-5504.

CHOWERS, M. Y., SPINA, C. A., KWOH, T. J., FITCH, N. J., RICHMAN, D. D., and GUATELLI, J. C. (1994). Optimal infectivity in vitro of human immunodeficiency virus type 1 requires an intact nef gene. J. Virol. 68, 2906-2914.

CONLON, K. C., OCHOA, A. C., KOPP, W. C., ORTALDO, J. R., URBA, W. J., LONGO, D. L., and YOUNG, H. A. (1992). Enhanced lymphokine production and lymphokine receptor expression in multiple antibody-stimulated human CD4+ peripheral blood lymphocytes. J. Immunol. 149, 3278-3289.

CUTURI, M. C., MURPHY, M., COSTA-GIOMI, M. P., WEINMANN, R., PERUSSIA, B., and TRINCHIERI, G. (1987). Independent regulation of tumor necrosis factor and lymphotoxin production by human peripheral blood lymphocytes. J. Exp. Med. 65, 1581-1594.

D'ALOJA, P., SANTARCANGELO, A. C., AROLD, S., BAUR, A., and FEDERICO, M. (2001). Genetic and functional analysis of the human immunodeficiency virus (HIV) type 1-inhibiting F12-HIV nef allele. J. Gen. Virol. 82, 2735-2745.

D'ALOJA, P., OLIVETTA, E., BONA, R., NAPPI, F., PEDACCHIA, D., PUGLIESE, K., FERRARI, G., VERANI, P., and FEDERICO, M. (1998). gag, vif, and nef genes contribute to the homologous viral interference induced by a nonproducer human immunodeficiency virus type 1 (HIV-1) variant: identification of novel HIV-1-inhibiting viral protein mutants. J. Virol. 72, 4308-4319.

DUH, E. J., MAURY, W. J., FOLKS, T. M., FAUCI, A. S., and RABSON, A. B. (1989). Tumor necrosis factor alpha activates human immunodeficiency virus type 1 through induction of nuclear factor binding to the NF-kappa B sites in the long terminal repeat. Proc. Natl. Acad. Sci. USA 86, 5974-5978.

DULL, T., ZUFFEREY, R., KELLY, M., MANDEL, R. J., NGUYEN, M., TRONO, D., and NALDINI, L. (1998). A third-generation lentivirus vector with a conditional packaging system. J. Virol. 72, 8463-8471.

EMERMAN, M., VAZEUX, R., and PEDEN, K. (1989). The rev gene product of the human immunodeficiency virus affects envelope-specific RNA localization. Cell 57, 1155-1165.

FACKLER, O. T., D'ALOJA, P., BAUR, A. S., FEDERICO, M., and PETERLIN, B. M. (2001). nef from human immunodeficiency virus type 1 (F12) inhibits viral production and infectivity. J. Virol. 75, 6601-6608.

FACKLER, O. T., LUO, W., GEYER, M., ALBERTS, A. S., and PETERLIN, B. M. (1999). Activation of Vav by Nef induces cytoskeletal rearrangements and downstream effector functions. Mol. Cell. 3, 729-739.

FEDERICO, M., TADDEO, B., CARLINI, F., NAPPI, F., VERANI, P., and ROSSI, G. B. (1993). A recombinant retrovirus carrying a non-producer human immunodeficiency virus (HIV) type 1 variant induces resistance to superinfecting HIV. J. Gen. Virol. 74, 2099-2110.

FEDERICO, M., NAPPI, F., BONA, R., D'ALOJA, P., VERANI, P., and ROSSI, G. B. (1995). Full expression of transfected nonproducer interfering HIV-1 proviral DNA abrogates susceptibility of human He—La CD4+ cells to HIV. Virology 206, 76-84.

FOLLENZI, A., AILLES, L. E., BAKOVIC, S., GEUNA, M., and NALDIM, L. (2000). Gene transfer by lentiviral vectors is limited by nuclear translocation and rescued by HIV-1 pol sequences. Nat. Genet. 25, 217-222.

FOX, B. A., WOFFENDIN, C., YANG, Z. Y., SAN, H., RANGA, U., GORDON, D., OSTERHOLZER, J., and NABEL, G. J. (1995). Genetic modification of human peripheral blood lymphocytes with a transdominant negative form of Rev: safety and toxicity. Hum. Gene Ther. 6, 997-1004.

FRAISER, C., ABRAHAM, D. A., VAN OIJEN, M., CUNLIFFE, V., IRVINE, A., CRAIG, R., and DZIERZAK, E. A. (1998). Inhibition of Tat-mediated transactivation and HIV replication with Tat mutant and repressor domain fusion proteins. Gene Ther. 5, 946-954.

GRIGNANI, F., KINSELLA, T., MENCARELLI, A., VALTIERI, M., RIGANELLI, D., GRIGNANI, F., LANFRANCONE, L., PESCHLE, C., NOLAN, G. P., and PELICCI, P. G. (1998). High-efficiency gene transfer and selection of human hematopoietic progenitor cells with a hybrid EBV/retroviral vector expressing the green fluorescence protein. Cancer Res. 58, 14-19.

HAMM, T. E., REKOSH, D., and H AMMARSKJOLD, M. L. (1999). Selection and characterization of human immunodeficiency virus type 1 mutants that are resistant to inhibition by the transdominant negative RevM10 protein. J. Virol. 73, 5741-5747.

JANG, S. K., and WIMMER, E. (1990). Cap-independent translation of encephalomyocarditis virus RNA: structural elements of the internal ribosomal entry site and involvement of a cellular 57-kD RNA-binding protein. Genes Dev. 4, 1560-1572.

JIA, L., JLANG, X. R., RAZAK, K., WU, Y. L., NEWLAND, A. C., and KELSEY, S. M. (1995). TNF-mediated killing of human leukaemic cells: effects of endogenous antioxidant levels and TNF alpha expression in leukaemic cell lines. Leuk. Res. 19, 187-194.

LAVIGNE, C., and THIERRY, A. R. (1997). Enhanced antisense inhibition of human immunodeficiency virus type 1 in cell cultures by DLS delivery system. Biochem. Biophys. Res. Commun. 237, 566-571.

LINDSTEIN, T., JUNE, C. H., LEDBETTER, J. A., STELLA, G., and THOMPSON, C. B. (1989). Regulation of lymphokine messenger RNA stability by a surface-mediated T cell activation pathway. Science 244, 339-343.

LIU, J., WOFFENDIN, C., YANG, Z. Y., and NABEL, G. J. (1994). Regulated expression of a dominant negative form of Rev improves resistance to HIV replication in T cells. Gene Ther. 1, 32-37.

LU, X., YU, H., LIU, S. H., BRODSKY, F. M., and PETERLIN, B. M. (1998). Interactions between HIV-1 Nef and vacuolar ATPase facilitate the internalization of CD4. Immunity 8, 647-656.

MALIM, M. H., HAUBER, J., LE, S. Y., MAIZEL, J. V., and CULLEN, B. R. (1989). The HIV-1 rev trans-activator acts through a structured target sequence to activate nuclear export of unspliced viral mRNA. Nature 338, 254-257.

MANGASARIAN, A., FOTI, M., AIKEN, C., CHIN, D., CARPENTIER, J. L., and TRONO, D. (1997). The HIV-1 Nef protein acts as a connector with sorting pathways in the Golgi and at the plasma membrane. Immunity 6, 67-77.

MAUTINO, M. R., KEISER, N., and MORGAN, R. A. (2001). Inhibition of human immunodeficiency virus type 1 (HIV-1) replication by HIV-1-based lentivirus vectors expressing transdominant Rev. J. Virol. 75, 3590-3599.

MAVILIO, F., FERRARI, G., ROSSIGNI, S., NOBILI, N., BONINI, C., CASORATI, G., TRAVERSARI, C., and BORDIGNON, C. (1994). Peripheral blood lymphocytes as target cells of retroviral vector-mediated gene transfer. Blood 83, 1988-1997.

MHASHILKAR, A. M., BAGLEY, J., CHEN, S. Y., SZILVAY, A. M., HELLAND, D. G., and MARASCO, W. A. (1995). Inhibition of HIV-1 Tat-mediated LTR transactivation and HIV-1 infection by anti-Tat single chain intrabodies. EMBO J. 14, 1542-1551.

MHASHILKAR, A. M., LAVECCHIO, J., EBERHARDT, B., PORTER-BROOKS, J., BOISOT, S., DOVE, J. H., PUMPHREY, C., LI, X., WEISSMAHR, R. N., RING, D. B., RAMSTEDT, U., and MARASCO, W. A. (1999). Inhibition of human immunodeficiency virus type 1 replication in vitro in acutely and persistently infected human CD4+ mononuclear cells expressing murine and humanized anti-human immunodeficiency virus type 1 tat single-chain variable fragment intrabodies. Hum. Gene Ther. 10, 1453-1467.

NALDINI, L., BLOMER, U., GALLAY, P., ORY, D., MULLIGAN, R., GAGE, F. H., VERMA, I. M., and TRONO, D. (1996). In vivo gene delivery and stable transduction of nondividing cells by a lentiviral vector. Science 272, 263-267.

NUNN, M. F., and MARSH, J. W. (1996). Human immunodeficiency virus type 1 Nef associates with a member of the p21-activated kinase family. J. Virol. 70, 6157-6161.

OLIVETTA, E., PUGLIESE, K., BONA, R., D'ALOJA, P., FERRANTELLI, F., SANTARCANGELO, A. C., MATTIA, G., VERANI, P., and FEDERICO, M. (2000). cis expression of the F12 human immunodeficiency virus (HIV) Nef allele transforms the highly productive NL4-3 HIV type 1 to a replication-defective strain: involvement of both Env gp41 and CD4 intracytoplasmic tails. J. Virol. 74, 483-492.

PIGUET, V., CHEN, Y. L., MANGASARIAN, A., FOTI, M., CARPENTIER, J. L., and TRONO, D. (1998). Mechanism of Nef-induced CD4 endocytosis: Nef connects CD4 with the mu chain of adaptor complexes. EMBO J. 17, 2472-2481.

PLAVEC, I., AGARWAL, M., HO, K. E., PINEDA, M., AUTEN, J., MATSUZAKI, H., ESCAICH, S., BONY-HADI, M., BOHNLEIN, E., and HAMM, T. E. (1997). High trasndominant RevM10 protein levels are required to inhibit HIV-1 replication in cell lines and primary T cells: implication for gene therapy of AIDS. Gene Ther. 4, 128-139.

R E, F., and LUBAN, J. (1997). HIV-1 Vpr: G2 cell cycle arrest, macrophages and nuclear transport. Prog. Cell Cycle Res. 3, 21-27.

RENKEMA, G. H., MANNINEN, A., MANN, D. A., HARRIS, M., and SAKSELA, K. (1999). Identification of the Nef-associated kinase as p21-activated kinase 2. Curr. Biol. 9, 1407-1410.

ROEBUCK, K. A., and SAIFUDDIN, M. (1999). Regulation of HIV-1 transcription. Gene Expr. 8, 67-84.

ROSSI, C., BALBONI, P. G., BETTI, M., MARCONI, P. C., BOZZINI, R., GROSSI, M. P., BARBANTI-BRODANO, G., and CAPUTO, A. (1997). Inhibition of HIV-1 replication by a Tat transdominant negative mutant in human peripheral blood lymphocytes from healthy donors and HIV-1-infected patients. Gene Ther. 4, 1261-1269.

ROSSI, G. B., VERANI, P., MACCHI, B., FEDERICO, M., ORECCHIA, A., NICOLETTI, L., BUTTO, S., LAZZARIN, A., MARIANI, G., IPPOLITO, G., and MANNARI, V. (1987). Recovery of HIV-related retroviruses from Italian patients with AIDS or AIDS-related complex and from asymptomatic at-risk individuals. Ann. NY Acad. Sci. 511, 390-400.

ROSSI, J. J. (2000). Ribozyme therapy for HIV infection. Adv. Drug Deliv. Rev. 44, 71-78.

SAWAI, E. T., BAUR, A., STRUBLE, H., PETERLIN, B. M., LEVY, J. A., and CHENG-MAYER, C. (1994). Human immunodeficiency virus type 1 Nef associates with a cellular serine kinase in T lymphocytes. Proc. Natl. Acad. Sci. USA 91, 1539-1543.

SAWAI, E. T., BAUR, A. S., PETERLIN, B. M., LEVY, J. A., and CHENG-MAYER, C. (1995). A conserved domain and membrane targeting of Nef from HIV and SIV are required for association with a cellular serine kinase activity. J. Biol. Chem. 270, 15307-15314.

SHAHABUDDIN, M., and KHAN, A. S. (2000). Inhibition of human immunodeficiency virus type 1 by packageable, multigenic antisense RNA. Antisense Nucleic Acid Drug Dev. 10, 141-151.

SUBBRAMANIAN, R. A., KESSOUS-ELBAZ, A., LODGE, R., FORGET, J., YAO, X. J., BERGERON, D., and COHEN, E. A. (1998). Human immunodeficiency virus type 1 Vpr is a positive regulator of viral transcription and infectivity in primary human macrophages. J. Exp. Med. 187, 1103-1111.

SUNG, S. S., BJORNDAHAL, J. M., WANG, C. Y., KAO, H. T., and F U, S. M. (1988). Production of tumor necrosis factor/cachectin by human T cell lines and peripheral blood T lymphocytes stimulated by phorbol myristate acetate and anti-CD3 antibody. J. Exp. Med. 167, 937-953.

THEODORE, T. S., ENGLUND, G., BUCKLER-WHITE, A., BUCKLER, C. E., MARTIN, M. A., and PEDEN, K. W. (1996). Construction and characterization of a stable full-length macrophage-tropic HIV type 1 molecular clone that directs the production of high titers of progeny virions. AIDS Res. Hum. Retroviruses 12, 191-194.

VODICKA, M. A., KOEPP, D. M., SILVER, P. A., and EMERMAN, M. (1998). HIV-1 Vpr interacts with the nuclear transport pathway to promote macrophage infection. Genes Dev. 12, 175-185.

WIGLER, M., SWEET, R., SIM, G. K., WOLD, B., PELLICER, A., LACY, E., MANIATIS, T., SILVERSTEIN, S., and AXEL, R. (1979). Transformation of mammalian cells with genes from prokaryotes and eukaryotes. Cell 16, 777-785.

What is claimed is:

1. A polynucleotide encoding a fusion protein comprising a first sequence and a second sequence, wherein the first sequence of the fusion protein comprises at least the extracellular and transmembrane domains of human low affinity Nerve Growth Factor receptor (LNGFR), and the second sequence of the fusion protein comprises a mutant HIV Nef, wherein the mutant HIV Nef contains the following amino acid substitutions: G140E, V153L and E177G, and the mutant HIV Nef is encoded C-terminally to the LNGFR, wherein the mutant HIV Nef retains the ability to inhibit HIV-1 replication.

2. The polynucleotide according to claim 1 wherein the LNGFR forms the $NH_2$ part of the fusion protein encoded by said polynucleotide and the mutant HIV Nef forms the COOH part of the fusion protein encoded by said polynucleotide.

3. A retroviral vector comprising, and capable of expressing, the polynucleotide of claim 1 or 2.

4. The retroviral vector according to claim 3 wherein the expression vector is a lentiviral vector.

5. The retroviral vector according to claim 4 wherein the lentiviral vector is derived from an HIV vector.

6. A retroviral particle comprising the retroviral vector of claim 5.

7. A cell infected or transduced with the retroviral vector of claim 5.

8. A pharmaceutical composition comprising the retroviral vector of claim 5 and a pharmaceutically acceptable carrier, diluent or excipient.

9. A retroviral particle comprising the retroviral vector of claim 4.

10. A cell infected or transduced with the retroviral vector of claim 4.

11. A pharmaceutical composition comprising the retroviral vector of claim 4 and a pharmaceutically acceptable carrier, diluent or excipient.

12. A retroviral particle comprising the retroviral vector of claim 3.

13. The retroviral particle according to claim 12 wherein the particle is pseudotyped.

14. A cell infected or transduced with the retroviral particle of claim 12.

15. The cell according to claim 14 wherein the cell is a monocyte, macrophage, or lymphocyte.

16. A pharmaceutical composition comprising the retroviral particle of claim 12 and a pharmaceutically acceptable carrier, diluent or excipient.

17. A retroviral production kit for producing a retrovirus comprising the retroviral vector of claim 3 and a composition comprising retroviral gag-pol and Env proteins.

18. The retroviral production kit of claim 17 wherein the retroviral vector further comprises an expressible sequence that encodes at least part of the sequence from a HIV pol polypurine tract (PPT).

19. A retroviral particle produced by the retroviral production kit of claim 18.

20. A retroviral production kit for producing a retrovirus comprising
    (a) a vector comprising the retroviral vector of claim 3;
    (b) a vector comprising a polynucleotide sequence encoding a retroviral gag-pol protein; and
    (c) a vector comprising a polynucleotide sequence encoding a retroviral Env protein.

21. A retroviral particle produced by the retroviral production kit of claim 20.

22. A cell infected or transduced with the retroviral vector of claim 3.

23. The cell according to claim 22 wherein the cell is a monocyte, macrophage, or lymphocyte.

24. A pharmaceutical composition comprising the retroviral vector of claim 3 and a pharmaceutically acceptable carrier, diluent or excipient.

25. A cell infected or transduced with the polynucleotide of claim 1 or 2.

26. The cell according to claim 25 wherein the cell is a monocyte, macrophage, or a lymphocyte.

27. A pharmaceutical composition comprising the cell according to claim 25 and a pharmaceutically acceptable carrier, diluent or excipient.

28. A pharmaceutical composition comprising the polynucleotide of claim 1 or 2 and a pharmaceutically acceptable carrier, diluent or excipient.

* * * * *

```
                              SEQUENCE LISTING

<160> NUMBER OF SEQ ID NOS: 9

<210> SEQ ID NO 1
<211> LENGTH: 427
<212> TYPE: PRT
<213> ORGANISM: Homo sapiens

<400> SEQUENCE: 1

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn
            35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
            115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
            195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg Trp Asn Ser Cys Lys Gln Asn Lys Gln Gly Ala Asn Ser Arg
            275                 280                 285

Pro Val Asn Gln Thr Pro Pro Pro Glu Gly Glu Lys Leu His Ser Asp
    290                 295                 300

Ser Gly Ile Ser Val Asp Ser Gln Ser Leu His Asp Gln Gln Pro His
```

-continued

```
            305                 310                 315                 320
        Thr Gln Thr Ala Ser Gly Gln Ala Leu Lys Gly Asp Gly Gly Leu Tyr
                        325                 330                 335
        Ser Ser Leu Pro Pro Ala Lys Arg Glu Glu Val Glu Lys Leu Leu Asn
                        340                 345                 350
        Gly Ser Ala Gly Asp Thr Trp Arg His Leu Ala Gly Glu Leu Gly Tyr
                        355                 360                 365
        Gln Pro Glu His Ile Asp Ser Phe Thr His Glu Ala Cys Pro Val Arg
                    370                 375                 380
        Ala Leu Leu Ala Ser Trp Ala Thr Gln Asp Ser Ala Thr Leu Asp Ala
        385                 390                 395                 400
        Leu Leu Ala Ala Leu Arg Arg Ile Gln Arg Ala Asp Leu Val Glu Ser
                        405                 410                 415
        Leu Cys Ser Glu Ser Thr Ala Thr Ser Pro Val
                        420                 425

<210> SEQ ID NO 2
<211> LENGTH: 1004
<212> TYPE: DNA
<213> ORGANISM: Artificial sequence
<220> FEATURE:
<223> OTHER INFORMATION: Truncated human LNGFR gene

<400> SEQUENCE: 2
aattcgggcc gcggccagct ccggcgggca gggggggcgc tggagcgcag cgcagcgcag     60
ccccatcagt ccgcaaagcg gaccgagctg gaagtcgagc gctgccgcgg gaggcgggcg    120
atgggggcag gtgccaccgg ccgcgccatg gacgggccgc cctgctgct gttgctgctt     180 ctgggggtgt cccttggagg tgccaaggag gcatgcccca caggcctgta cacacacagc    240
ggtgagtgct gcaaagcctg caacctgggc gagggtgtgg cccagccttg tggagccaac    300
cagaccgtgt gtgagccctg cctggacagc gtgacgttct ccgacgtggt gagcgcgacc    360
gagccgtgca agccgtgcac cgagtgcgtg gggctccaga gcatgtcggc gccgtgcgtg    420
gaggccgacg acgccgtgtg ccgctgcgcc tacggctact accaggatga gacgactggg    480
cgctgcgagg cgtgccgcgt gtgcgaggcg ggctcgggcc tcgtgttctc ctgccaggac    540
aagcagaaca ccgtgtgcga ggagtgcccc gacggcacgt attccgacga ggccaaccac    600
gtggacccgt gcctgccctg caccgtgtgc gaggacaccg agcgccagct ccgcgagtgc    660
acacgctggg ccgacgccga gtgcgaggag atccctggcc gttggattac acggtccaca    720
cccccagagg gctcggacag cacagccccc agcacccagg agcctgaggc acctccagaa    780
caagacctca tagccagcac ggtggcaggt gtggtgacca cagtgatggg cagctcccag    840
cccgtggtga cccgaggcac caccgacaac ctcatccctg tctattgctc catcctggct    900
gctgtggttg tgggccttgt ggcctacata gccttcaaga ggtggaacag ggggatcctc    960
tagagtcggc tgggtgtggc ggaccgctat caggacatag cgtt                   1004

<210> SEQ ID NO 3
<211> LENGTH: 1464
<212> TYPE: DNA
<213> ORGANISM: artificial sequence
<220> FEATURE:
<223> OTHER INFORMATION: Delta LNGFR-Nef F12 fusion DNA

<400> SEQUENCE: 3
atgggggcag gtgccaccgg ccgcgccatg gacgggccgc cctgctgct gttgctgctt     60
```

-continued

```
ctgggggtgt cccttggagg tgccaaggag gcatgcccca caggcctgta cacacacagc    120
ggtgagtgct gcaaagcctg caacctgggc gagggtgtgg cccagccttg tggagccaac    180
cagaccgtgt gtgagccctg cctggacagc gtgacgttct ccgacgtggt gagcgcgacc    240
gagccgtgca agccgtgcac cgagtgcgtg gggctccaga gcatgtcggc gccgtgcgtg    300
gaggccgacg acgccgtgtg ccgctgcgcc tacggctact accaggatga gacgactggg    360
cgctgcgagg cgtgccgcgt gtgcgaggcg ggctcgggcc tcgtgttctc ctgccaggac    420
aagcagaaca ccgtgtgcga ggagtgcccc gacggcacgt attccgacga ggccaaccac    480
gtggacccgt gcctgccctg caccgtgtgc gaggacaccg agcgccagct ccgcgagtgc    540
acacgctggg ccgacgccga gtgcgaggag atccctggcc gttggattac acggtccaca    600
cccccagagg gctcggacag cacagccccc agcacccagg agcctgaggc acctccagaa    660
caagacctca tagccagcac ggtggcaggt gtggtgacca cagtgatggg cagctcccag    720
cccgtggtga cccgaggcac caccgacaac ctcatccctg tctattgctc catcctggct    780
gctgtggttg tgggccttgt ggcctacata gccttcaaga ggtggaacag gggaatcgtc    840
atgggtggca agtggtcaaa aagtagtgtg gttggatggc ctgctgtaag ggaaagaatg    900
agacgagctg agccagcagc agatggggtg ggagcagcat ctcgagacct agaaaaacat    960
ggagcaatca aagtagcaa tacagcagct accaatgctg attgtgcctg gctagaagca   1020
caagaggagg aggaggtggg ttttccagtc acacctcagg tacctttaag accaatgact   1080
tacaaggcag ctgtagatct tagccacttt ttaaaagaaa agggggact ggaaggacta   1140 attcactccc aacgaagaca agatatcctt gatctgtgga tctaccacac acaaggctac   1200
ttccctgatt ggcagaacta cacaccagga ccagggatca gatatccact gacctttgaa   1260
tggtgctaca agcgagtacc agttgagcca gagaagttag aagaagccaa caaggagag   1320 aacaccagct tgttacaccc tgtgagcctg catggaatgg atgacccggg gagagaagtg   1380
ttagagtgga ggtttgacag ccgcctagca tttcatcacg tggcccgaga gctgcatccg   1440
gagtacttca agaactgctg atga                                           1464
```

<210> SEQ ID NO 4
<211> LENGTH: 333
<212> TYPE: PRT
<213> ORGANISM: Artificial sequence
<220> FEATURE:
<223> OTHER INFORMATION: Truncated Human LNGFR protein

<400> SEQUENCE: 4

```
Asn Ser Gly Arg Gly Gln Leu Arg Arg Ala Gly Gly Ala Leu Glu Arg
1               5                   10                  15

Ser Ala Ala Gln Pro His Gln Ser Ala Lys Arg Thr Glu Leu Glu Val
            20                  25                  30

Glu Arg Cys Arg Gly Arg Ala Met Gly Ala Gly Ala Thr Gly Arg
        35                  40                  45

Ala Met Asp Gly Pro Arg Leu Leu Leu Leu Leu Leu Gly Val Ser
    50                  55                  60

Leu Gly Gly Ala Lys Glu Ala Cys Pro Thr Gly Leu Tyr Thr His Ser
65                  70                  75                  80

Gly Glu Cys Cys Lys Ala Cys Asn Leu Gly Glu Gly Val Ala Gln Pro
                85                  90                  95

Cys Gly Ala Asn Gln Thr Val Cys Glu Pro Cys Leu Asp Ser Val Thr
            100                 105                 110
```

```
Phe Ser Asp Val Val Ser Ala Thr Glu Pro Cys Lys Pro Cys Thr Glu
            115                 120                 125

Cys Val Gly Leu Gln Ser Met Ser Ala Pro Cys Val Glu Ala Asp Asp
    130                 135                 140

Ala Val Cys Arg Cys Ala Tyr Gly Tyr Tyr Gln Asp Glu Thr Thr Gly
145                 150                 155                 160

Arg Cys Glu Ala Cys Arg Val Cys Glu Ala Gly Ser Gly Leu Val Phe
                165                 170                 175

Ser Cys Gln Asp Lys Gln Asn Thr Val Cys Glu Glu Cys Pro Asp Gly
            180                 185                 190

Thr Tyr Ser Asp Glu Ala Asn His Val Asp Pro Cys Leu Pro Cys Thr
            195                 200                 205

Val Cys Glu Asp Thr Glu Arg Gln Leu Arg Glu Cys Thr Arg Trp Ala
    210                 215                 220

Asp Ala Glu Cys Glu Glu Ile Pro Gly Arg Trp Ile Thr Arg Ser Thr
225                 230                 235                 240

Pro Pro Glu Gly Ser Asp Ser Thr Ala Pro Ser Thr Gln Glu Pro Glu
                245                 250                 255

Ala Pro Pro Glu Gln Asp Leu Ile Ala Ser Thr Val Ala Gly Val Val
            260                 265                 270

Thr Thr Val Met Gly Ser Ser Gln Pro Val Val Thr Arg Gly Thr Thr
            275                 280                 285

Asp Asn Leu Ile Pro Val Tyr Cys Ser Ile Leu Ala Ala Val Val Val
    290                 295                 300

Gly Leu Val Ala Tyr Ile Ala Phe Lys Arg Trp Asn Arg Gly Ile Leu
305                 310                 315                 320

Ser Arg Leu Gly Val Ala Asp Arg Tyr Gln Asp Ile Ala
                325                 330

<210> SEQ ID NO 5
<211> LENGTH: 206
<212> TYPE: PRT
<213> ORGANISM: Human immunodeficiency virus type 1 F12

<400> SEQUENCE: 5

Met Gly Gly Lys Trp Ser Lys Ser Ser Val Val Gly Trp Pro Ala Val
1               5                   10                  15

Arg Glu Arg Met Arg Arg Ala Glu Pro Ala Ala Asp Gly Val Gly Ala
                20                  25                  30

Ala Ser Arg Asp Leu Glu Lys His Gly Ala Ile Thr Ser Ser Asn Thr
            35                  40                  45

Ala Ala Thr Asn Ala Asp Cys Ala Trp Leu Glu Ala Gln Glu Glu Glu
        50                  55                  60

Glu Val Gly Phe Pro Val Thr Pro Gln Val Pro Leu Arg Pro Met Thr
65                  70                  75                  80

Tyr Lys Ala Ala Val Asp Leu Ser His Phe Leu Lys Glu Lys Gly Gly
                85                  90                  95

Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Thr
        115                 120                 125

Pro Gly Pro Gly Ile Arg Tyr Pro Leu Thr Phe Glu Trp Cys Tyr Lys
    130                 135                 140

Arg Val Pro Val Glu Pro Glu Lys Leu Glu Glu Ala Asn Lys Gly Glu
145                 150                 155                 160
```

```
Asn Thr Ser Leu Leu His Pro Val Ser Leu His Gly Met Asp Asp Pro
            165                 170                 175

Glu Arg Glu Val Leu Glu Trp Arg Phe Asp Ser Arg Leu Ala Phe His
        180                 185                 190

His Val Ala Arg Glu Leu His Pro Glu Tyr Phe Lys Asn Cys
            195                 200                 205

<210> SEQ ID NO 6
<211> LENGTH: 486
<212> TYPE: PRT
<213> ORGANISM: artificial sequence
<220> FEATURE:
<223> OTHER INFORMATION: delta LNGFR-Nef F12 fusion protein

<400> SEQUENCE: 6

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
            20                  25                  30

Pro Thr Gly Leu Tyr Thr His Ser Gly Glu Cys Cys Lys Ala Cys Asn
        35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Val Gly Leu Val Ala Tyr Ile Ala Phe
            260                 265                 270

Lys Arg Trp Asn Arg Gly Ile Val Met Gly Gly Lys Trp Ser Lys Ser
        275                 280                 285

Ser Val Val Gly Trp Pro Ala Val Arg Glu Arg Met Arg Arg Ala Glu
    290                 295                 300

Pro Ala Ala Asp Gly Val Gly Ala Ala Ser Arg Asp Leu Glu Lys His
305                 310                 315                 320
```

```
Gly Ala Ile Thr Ser Ser Asn Thr Ala Ala Thr Asn Ala Asp Cys Ala
            325                 330                 335

Trp Leu Glu Ala Gln Glu Glu Glu Val Gly Phe Pro Val Thr Pro
        340                 345                 350

Gln Val Pro Leu Arg Pro Met Thr Tyr Lys Ala Ala Val Asp Leu Ser
            355                 360                 365

His Phe Leu Lys Glu Lys Gly Leu Glu Gly Leu Ile His Ser Gln
        370                 375                 380

Arg Arg Gln Asp Ile Leu Asp Leu Trp Ile Tyr His Thr Gln Gly Tyr
385                 390                 395                 400

Phe Pro Asp Trp Gln Asn Tyr Thr Pro Gly Pro Gly Ile Arg Tyr Pro
                405                 410                 415

Leu Thr Phe Glu Trp Cys Tyr Lys Arg Val Pro Val Glu Pro Glu Lys
            420                 425                 430

Leu Glu Glu Ala Asn Lys Gly Glu Asn Thr Ser Leu Leu His Pro Val
        435                 440                 445

Ser Leu His Gly Met Asp Asp Pro Glu Arg Glu Val Leu Glu Trp Arg
    450                 455                 460

Phe Asp Ser Arg Leu Ala Phe His His Val Ala Arg Glu Leu His Pro
465                 470                 475                 480

Glu Tyr Phe Lys Asn Cys
            485

<210> SEQ ID NO 7
<211> LENGTH: 3386
<212> TYPE: DNA
<213> ORGANISM: Homo sapiens

<400> SEQUENCE: 7
gccgcggcca gctccggcgg gcagggggg cgctggagcg cagcgcagcg cagccccatc     60
agtccgcaaa gcggaccgag ctggaagtcg agcgctgccg cgggaggcgg gcgatggggg    120
caggtgccac cggccgcgcc atggacgggc gcgcctgct gctgttgctg cttctggggg     180
tgtcccttgg aggtgccaag gaggcatgcc ccacaggcct gtacacacac agcggtgagt    240
gctgcaaagc ctgcaacctg ggcgagggtg tggcccagcc ttgtggagcc aaccagaccg    300
tgtgtgagcc ctgcctggac agcgtgacgt tctccgacgt ggtgagcgcg accgagccgt    360
gcaagccgtg caccgagtgc gtggggctcc agagcatgtc ggcgccgtgc gtggaggccg    420
acgacgccgt gtgccgctgc gcctacggct actaccagga tgagacgact gggcgctgcg    480
aggcgtgccg cgtgtgcgag gcgggctcgg gcctcgtgtt ctcctgccag gacaagcaga    540
acaccgtgtg cgaggagtgc cccgacggca cgtattccga cgaggccaac cacgtggacc    600
cgtgcctgcc ctgcaccgtg tgcgaggaca ccgagcgcca gctccgcgag tgcacacgct    660
gggccgacgc cgagtgcgag gagatccctg gccgttggat tacacggtcc acaccccag    720 agggctcgga cagcacagcc cccagcaccc aggagcctga ggcacctcca gaacaagacc    780
tcatagccag cacggtggca ggtgtggtga ccacagtgat gggcagctcc agcccgtgg    840 tgacccgagg caccaccgac aacctcatcc ctgtctattg ctccatcctg gctgctgtgg    900
ttgtgggcct tgtggcctac atagccttca agaggtggaa cagctgcaag cagaacaagc    960
aaggagccaa cagccggcca gtgaaccaga cgccccacc agagggagaa aaactccaca   1020
gcgacagtgg catctccgtg gacagccaga gcctgcatga ccagcagccc acacgcagca   1080
cagcctcggg ccaggccctc aagggtgacg gaggcctcta cagcagcctg ccccagcca   1140
```

```
agcgggagga ggtggagaag cttctcaacg gctctgcggg ggacacctgg cggcacctgg    1200
cgggcgagct gggctaccag cccgagcaca tagactcctt tacccatgag gcctgccccg    1260
ttcgcgccct gcttgcaagc tgggccaccc aggacagcgc cacactggac gccctcctgg    1320
ccgccctgcg ccgcatccag cgagccgacc tcgtggagag tctgtgcagt gagtccactg    1380
ccacatcccc ggtgtgagcc aaccggggga gcccccgccc cgcccacat tccgacaacc     1440 gatgctccag ccaacccctg tggagcccgc accccaccc tttgggggg gcccgcctgg      1500 cagaactgag ctcctctggg caggacctca gagtccaggc cccaaaacca cagccctgtc    1560
agtgcagccc gtgtggcccc ttcacttctg accacacttc ctgtccagag agagaagtgc    1620
ccctgctgcc tccccaaccc tgccctgcc cgtcaccat tcaggccac ctgccccctt       1680 ctcccacact gctaggtggg ccagcccctc ccaccacagc aggtgtcata tatggggggc    1740
caacaccagg gatggtacta ggggaagtg acaaggcccc agagactcag agggaggaat     1800
cgaggaacca gagccatgga ctctacactg tgaacttggg gaacaagggt ggcatcccag    1860
tggcctcaac cctccctcag cccctcttgc ccccacccc agcctaagat gaagaggatc     1920
ggaggcttgt cagagctggg aggggttttc gaagctcagc ccacccccct cattttggat    1980
ataggtcagt gaggcccagg gagaggccat gattcgccca agccagaca gcaacgggga     2040 ggccaagtgc aggctggcac cgccttctct aaatgagggg cctcaggttt gcctgagggc    2100
gaggggaggg tggcaggtga ccttctggga aatggcttga agccaagtca gctttgcctt    2160
ccacgctgtc tccagacccc caccccttcc ccactgcctg cccacccgtg gagatgggat    2220
gcttgcctag ggcctggtcc atgatggagt caggtttggg gttcgtggaa agggtgctgc    2280
ttccctctgc ctgtccctct caggcatgcc tgtgtgacat cagtggcatg gctccagtct    2340
gctgccctcc atcccgacat ggacccggag ctaacactgg cccctagaat cagcctaggg    2400
gtcagggacc aaggaccccct caccttgcaa cacacagaca cacgcacaca cacacacagg   2460
aggagaaatc tcactttcct ccatgagttt tttctcttgg gctgagactg gatactgccc    2520
ggggcagctg ccagagaagc atcggaggga attgaggtct gctcggccgt cttcactcgc    2580 ccccggggttt ggcgggccaa ggactgccga ccgaggctgg agctggcgtc tgtcttcaag   2640
ggcttacacg tggaggaatg ctcccccatc ctccccttcc ctgcaaacat ggggttggct    2700
gggcccagaa ggttgcgatg aagaaaagcg ggccagtgtg ggaatgcggc aagaaggaat    2760
tgacttcgac tgtgacctgt ggggatttct cccagctcta gacaaccctg caaaggactg    2820
ttttttcctg agcttggcca gagggggcc atgaggcctc agtggacttt ccaccccctc     2880
cctggcctgt tctgttttgc ctgaagttgg agtgagtgtg gctccctct atttagcatg     2940 acaagcccca ggcaggctgt cgctgacaa ccaccgctcc ccagcccagg gttccccag     3000 ccctgtggaa gggactagga gcactgtagt aaatggcaat tctttgacct caacctgtga    3060
tgaggggagg aaactcacct gctggcccct cacctgggca cctggggagt gggacagagt    3120
ctgggtgtat ttattttcct ccccagcagg tggggagggg gtttggtggc ttgcaagtat    3180
gttttagcat gtgtttggtt ctggggcccc ttttactcc ccttgagctg agatggaacc     3240
cttttggccc ccagctgggg gccatgagct ccagaccccc agcaacctc ctatcacctc     3300 ccctccttgc ctcctgtgta atcatttctt gggccctcct gaaacttaca cacaaaacgt    3360
taagtgatga acattaaata gcaaag                                         3386
```

<210> SEQ ID NO 8

```
<211> LENGTH: 624
<212> TYPE: DNA
<213> ORGANISM: Artificial sequence
<220> FEATURE:
<223> OTHER INFORMATION: Nef F12 mutant used to make fusion protein

<400> SEQUENCE: 8
atgggtggca agtggtcaaa aagtagtgtg gttggatggc ctgctgtaag ggaaagaatg      60
agacgagctg agccagcagc agatggggtg ggagcagcat ctcgagacct agaaaaacat     120
ggagcaatca caagtagcaa tacagcagct accaatgctg attgtgcctg gctagaagca     180
caagaggagg aggaggtggg ttttccagtc acacctcagg taccttaag accaatgact     240 tacaaggcag ctgtagatct tagccacttt ttaaaagaaa agggggact ggaaggacta      300 attcactccc aacgaagaca agatatcctt gatctgtgga tctaccacac aaggctac      360 ttccctgatt ggcagaacta cacaccagga ccagggatca gatatccact gacctttgaa     420
tggtgctaca gcgagtacc agttgagcca gagaagttag aagaagccaa caaggagag      480 aacaccagct tgttacaccc tgtgagcctg catggaatgg atgacccggg gagagaagtg     540
ttagagtgga ggtttgacag ccgcctagca tttcatcacg tggcccgaga gctgcatccg     600
gagtacttca agaactgctg atga                                            624

<210> SEQ ID NO 9
<211> LENGTH: 206
<212> TYPE: PRT
<213> ORGANISM: Artificial sequence
<220> FEATURE:
<223> OTHER INFORMATION: Nef F12 mutant used to make fusion protein

<400> SEQUENCE: 9

Met Gly Gly Lys Trp Ser Lys Ser Ser Val Val Gly Trp Pro Ala Val
1               5                   10                  15

Arg Glu Arg Met Arg Arg Ala Glu Pro Ala Ala Asp Gly Val Gly Ala
            20                  25                  30

Ala Ser Arg Asp Leu Glu Lys His Gly Ala Ile Thr Ser Ser Asn Thr
        35                  40                  45

Ala Ala Thr Asn Ala Asp Cys Ala Trp Leu Glu Ala Gln Glu Glu Glu
    50                  55                  60

Glu Val Gly Phe Pro Val Thr Pro Gln Val Pro Leu Arg Pro Met Thr
65                  70                  75                  80

Tyr Lys Ala Ala Val Asp Leu Ser His Phe Leu Lys Glu Lys Gly Gly
                85                  90                  95

Leu Glu Gly Leu Ile His Ser Gln Arg Arg Gln Asp Ile Leu Asp Leu
            100                 105                 110

Trp Ile Tyr His Thr Gln Gly Tyr Phe Pro Asp Trp Gln Asn Tyr Thr
        115                 120                 125

Pro Gly Pro Gly Ile Arg Tyr Pro Leu Thr Phe Glu Trp Cys Tyr Lys
    130                 135                 140

Arg Val Pro Val Glu Pro Glu Lys Leu Glu Glu Ala Asn Lys Gly Glu
145                 150                 155                 160

Asn Thr Ser Leu Leu His Pro Val Ser Leu His Gly Met Asp Asp Pro
                165                 170                 175

Gly Arg Glu Val Leu Glu Trp Arg Phe Asp Ser Arg Leu Ala Phe His
            180                 185                 190

His Val Ala Arg Glu Leu His Pro Glu Tyr Phe Lys Asn Cys
        195                 200                 205
```